(12) United States Patent
Cabrera et al.

(10) Patent No.: US 12,733,934 B2
(45) **Date of Patent: *Sep. 15, 2026**

(54) ADAPTER, EXTENSION, AND CONNECTOR ASSEMBLIES FOR SURGICAL DEVICES

(71) Applicant: Covidien LP, Mansfield, MA (US)

(72) Inventors: Ramiro Cabrera, Cheshire, CT (US); Anne Nelson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/066,997

(22) Filed: Feb. 28, 2025

(65) Prior Publication Data

US 2025/0261945 A1 Aug. 21, 2025

Related U.S. Application Data

(60) Continuation of application No. 17/878,131, filed on Aug. 1, 2022, now Pat. No. 12,262,893, which is a (Continued)

(51) Int. Cl.
*A61B 17/00* (2006.01)
*A61B 17/115* (2006.01)

(52) U.S. Cl.
CPC . *A61B 17/1155* (2013.01); *A61B 2017/00367* (2013.01); *A61B 2017/00398* (2013.01); (Continued)

(58) Field of Classification Search
CPC ...... A61B 17/1155; A61B 2017/00367; A61B 2017/00398; A61B 2017/0046; A61B 2017/00473; A61B 2017/00477
(Continued)

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CA 2824590 A1 4/2014
(Continued)

OTHER PUBLICATIONS

Examination Report received for Australian Patent Application No. 2014204542, mailed on Jan. 7, 2016, 3 pages.
(Continued)

*Primary Examiner* — Robert F Long

(57) ABSTRACT

An assembly including an adapter assembly and an extension assembly for connecting an end effector to an electrosurgical instrument is provided. The adapter assembly includes first and second pusher assemblies configured for converting rotational motion into linear motion and a drive member for transferring rotational motion. The extension assembly includes at least one flexible band assembly for transferring the linear motion from the adapter assembly and a trocar assembly configured for converting rotational motion into linear motion. Also provided is a connection assembly for connecting a first tubular member to a second tubular member.

18 Claims, 29 Drawing Sheets

Related U.S. Application Data continuation of application No. 16/262,242, filed on Jan. 30, 2019, now Pat. No. 11,399,836, which is a division of application No. 14/875,766, filed on Oct. 6, 2015, now Pat. No. 10,226,254.

(60) Provisional application No. 62/066,518, filed on Oct. 21, 2014.

(52) U.S. Cl.
CPC ................. *A61B 2017/0046* (2013.01); *A61B 2017/00473* (2013.01); *A61B 2017/00477* (2013.01)

(58) Field of Classification Search
USPC ......... 227/1–2, 8–19, 51, 63–64, 77–82, 99, 227/107, 140, 156; 606/139, 142, 143, 606/205–208
See application file for complete search history.

(56) References Cited

U.S. PATENT DOCUMENTS 3,111,328 A 11/1963 Di Rito et al.
3,651,720 A 3/1972 Indyk
3,695,058 A 10/1972 Keith, Jr.
3,734,515 A 5/1973 Dudek
3,759,336 A 9/1973 Marcovitz et al.
4,162,399 A 7/1979 Hudson
4,460,296 A * 7/1984 Sivertson, Jr. ........ B25B 33/005 408/239 R
4,473,077 A 9/1984 Noiles et al.
4,550,967 A * 11/1985 Riches ............... H01R 13/6278 439/345
4,606,343 A 8/1986 Conta et al.
4,705,038 A 11/1987 Sjostrom et al.
4,722,685 A 2/1988 De Estrada
4,823,807 A 4/1989 Russell et al.
4,874,181 A 10/1989 Hsu
5,098,134 A * 3/1992 Monckton ............. F16L 21/007 285/38
5,101,807 A * 4/1992 Kawashima ....... A61B 1/00126 600/112
5,129,118 A 7/1992 Walmesley
5,129,570 A 7/1992 Schulze et al.
5,152,744 A 10/1992 Krause et al.
5,205,459 A 4/1993 Brinkerhoff et al.
5,219,111 A * 6/1993 Bilotti .................. A61B 17/072 227/19
5,289,963 A * 3/1994 McGarry ........... A61B 17/0686 606/143
5,301,061 A 4/1994 Nakada et al.
5,312,023 A 5/1994 Green et al.
5,326,013 A 7/1994 Green et al.
5,350,104 A 9/1994 Main et al.
5,350,355 A 9/1994 Sklar
5,383,874 A 1/1995 Jackson et al.
5,383,880 A 1/1995 Hooven
5,389,098 A 2/1995 Tsuruta et al.
5,391,156 A 2/1995 Hildwein et al.
5,395,033 A 3/1995 Byrne et al.
5,400,267 A 3/1995 Denen et al.
5,411,508 A 5/1995 Bessler et al.
5,413,267 A 5/1995 Solyntjes et al.
5,427,087 A 6/1995 Ito et al.
5,433,721 A 7/1995 Hooven et al.
5,467,911 A 11/1995 Tsuruta et al.
5,476,379 A 12/1995 Disel
5,487,499 A 1/1996 Sorrentino et al.
5,518,163 A 5/1996 Hooven
5,518,164 A 5/1996 Hooven
5,526,822 A 6/1996 Burbank et al.
5,529,235 A 6/1996 Boiarski et al.
5,535,934 A 7/1996 Boiarski et al.
5,535,937 A 7/1996 Boiarski et al.
5,540,375 A 7/1996 Bolanos et al.
5,540,706 A 7/1996 Aust et al.
5,542,594 A 8/1996 Mckean et al.
5,549,637 A 8/1996 Crainich
5,553,675 A 9/1996 Pitzen et al.
5,562,239 A 10/1996 Boiarski et al.
5,564,615 A 10/1996 Bishop et al.
5,609,560 A 3/1997 Ichikawa et al.
5,626,587 A 5/1997 Bishop et al.
5,632,432 A 5/1997 Schulze et al.
5,645,209 A 7/1997 Green et al.
5,647,526 A 7/1997 Green et al.
5,653,374 A 8/1997 Young et al.
5,658,300 A 8/1997 Bito et al.
5,662,662 A 9/1997 Bishop et al.
5,667,517 A 9/1997 Hooven
5,693,042 A 12/1997 Boiarski et al.
5,704,534 A 1/1998 Huitema et al.
5,713,505 A 2/1998 Huitema
5,762,256 A * 6/1998 Mastri ................. A61B 17/072 227/176.1
5,762,603 A 6/1998 Thompson
5,765,652 A * 6/1998 Mathis .................... B25F 5/001 173/217
5,779,130 A 7/1998 Alesi et al.
5,782,396 A 7/1998 Mastri et al.
5,782,397 A 7/1998 Koukline
5,792,573 A 8/1998 Pitzen et al.
5,797,536 A 8/1998 Smith et al.
5,820,009 A 10/1998 Melling et al.
5,823,066 A * 10/1998 Huitema .......... A61B 17/07207 74/528
5,863,159 A 1/1999 Lasko
5,865,361 A * 2/1999 Milliman ............ A61B 17/068 227/176.1
5,908,427 A 6/1999 Mckean et al.
5,954,259 A 9/1999 Viola et al.
5,964,774 A 10/1999 Mckean et al.
5,993,454 A 11/1999 Longo
6,010,054 A 1/2000 Johnson et al.
6,017,354 A 1/2000 Culp et al.
6,032,849 A 3/2000 Mastri et al.
6,045,560 A 4/2000 Mckean et al.
6,090,123 A 7/2000 Culp et al.
6,126,651 A 10/2000 Mayer
6,129,547 A 10/2000 Cise et al.
6,165,169 A 12/2000 Panescu et al.
6,239,732 B1 5/2001 Cusey
6,241,139 B1 6/2001 Milliman et al.
6,264,086 B1 7/2001 Mcguckin, Jr.
6,264,087 B1 7/2001 Whitman
6,302,311 B1 10/2001 Adams et al.
6,315,184 B1 11/2001 Whitman
6,321,855 B1 11/2001 Barnes
6,329,778 B1 12/2001 Culp et al.
6,343,731 B1 2/2002 Adams et al.
6,348,061 B1 2/2002 Whitman
6,368,324 B1 4/2002 Dinger et al.
6,371,909 B1 4/2002 Hoeg et al.
6,434,507 B1 8/2002 Clayton et al.
6,443,973 B1 9/2002 Whitman
6,461,372 B1 10/2002 Jensen et al.
6,488,197 B1 12/2002 Whitman
6,491,201 B1 12/2002 Whitman
6,533,157 B1 3/2003 Whitman
6,537,280 B2 3/2003 Dinger et al.
6,610,066 B2 8/2003 Dinger et al.
6,611,793 B1 8/2003 Burnside et al.
6,645,218 B1 11/2003 Cassidy et al.
6,654,999 B2 12/2003 Stoddard et al.
6,681,979 B2 1/2004 Whitman
6,695,199 B2 2/2004 Whitman
6,698,643 B2 3/2004 Whitman
6,699,177 B1 3/2004 Wang et al.
6,716,233 B1 4/2004 Whitman
6,743,240 B2 6/2004 Smith et al.
6,783,533 B2 8/2004 Green et al.
6,792,390 B1 9/2004 Burnside et al.

(56) References Cited

U.S. PATENT DOCUMENTS 6,793,652 B1 9/2004 Whitman et al.
6,808,407 B1 * 10/2004 Cannon ................ H01R 13/625 439/314
6,817,508 B1 11/2004 Racenet et al.
6,821,282 B2 * 11/2004 Perry .................. A61B 17/115 606/1
6,830,174 B2 12/2004 Hillstead et al.
6,835,199 B2 12/2004 Mcguckin et al.
6,846,308 B2 1/2005 Whitman et al.
6,846,309 B2 1/2005 Whitman et al.
6,849,071 B2 2/2005 Whitman et al.
6,860,892 B1 3/2005 Tanaka et al.
6,899,538 B2 5/2005 Matoba
6,905,057 B2 6/2005 Swayze et al.
6,959,852 B2 11/2005 Shelton, IV et al.
6,964,363 B2 11/2005 Wales et al.
6,981,628 B2 1/2006 Wales
6,981,941 B2 1/2006 Whitman et al.
6,986,451 B1 1/2006 Mastri et al.
6,988,649 B2 1/2006 Shelton, IV et al.
7,032,798 B2 4/2006 Whitman et al.
RE39,152 E 6/2006 Aust et al.
7,055,731 B2 6/2006 Shelton, IV et al.
7,059,508 B2 6/2006 Shelton, IV et al.
7,077,856 B2 7/2006 Whitman
7,111,769 B2 9/2006 Wales et al.
7,122,029 B2 10/2006 Koop et al.
7,140,528 B2 11/2006 Shelton, IV
7,141,049 B2 11/2006 Stern et al.
7,143,923 B2 12/2006 Shelton, IV et al.
7,143,925 B2 12/2006 Shelton, IV et al.
7,143,926 B2 12/2006 Shelton, IV et al.
7,147,138 B2 12/2006 Shelton, IV
7,172,104 B2 2/2007 Scirica et al.
7,225,964 B2 6/2007 Mastri et al.
7,238,021 B1 7/2007 Johnson
7,246,734 B2 7/2007 Shelton, IV
7,252,660 B2 8/2007 Kunz
7,328,828 B2 2/2008 Ortiz et al.
7,364,060 B2 4/2008 Milliman
7,364,061 B2 4/2008 Swayze et al.
7,380,695 B2 6/2008 Doll et al.
7,380,696 B2 6/2008 Shelton, IV et al.
7,404,508 B2 7/2008 Smith et al.
7,407,078 B2 8/2008 Shelton, IV et al.
7,416,101 B2 8/2008 Shelton, IV et al.
7,419,080 B2 9/2008 Smith et al.
7,422,139 B2 9/2008 Shelton, IV et al.
7,431,189 B2 10/2008 Shelton, IV et al.
7,441,684 B2 10/2008 Shelton, IV et al.
7,448,525 B2 11/2008 Shelton, IV et al.
7,464,846 B2 12/2008 Shelton, IV et al.
7,464,847 B2 12/2008 Viola et al.
7,464,849 B2 12/2008 Shelton, IV et al.
7,481,347 B2 1/2009 Roy
7,481,824 B2 1/2009 Boudreaux et al.
7,487,899 B2 2/2009 Shelton, IV et al.
7,549,564 B2 6/2009 Boudreaux
7,565,993 B2 7/2009 Milliman et al.
7,568,603 B2 8/2009 Shelton, IV et al.
7,575,144 B2 8/2009 Ortiz et al.
7,588,175 B2 9/2009 Timm et al.
7,588,176 B2 9/2009 Timm et al.
7,637,409 B2 12/2009 Marczyk
7,641,093 B2 1/2010 Doll et al.
7,644,848 B2 1/2010 Swayze et al.
7,670,334 B2 3/2010 Hueil et al.
7,673,780 B2 3/2010 Shelton, IV et al.
7,699,835 B2 4/2010 Lee et al.
7,721,931 B2 5/2010 Shelton, IV et al.
7,738,971 B2 6/2010 Swayze et al.
7,740,159 B2 6/2010 Shelton, IV et al.
7,743,960 B2 6/2010 Whitman et al.
7,758,613 B2 7/2010 Whitman
7,766,210 B2 8/2010 Shelton, IV et al.
7,770,773 B2 8/2010 Whitman et al.
7,770,775 B2 8/2010 Shelton, IV et al.
7,793,812 B2 9/2010 Moore et al.
7,799,039 B2 9/2010 Shelton, IV et al.
7,802,712 B2 9/2010 Milliman et al.
7,803,151 B2 9/2010 Whitman
7,822,458 B2 10/2010 Webster, III et al.
7,845,534 B2 12/2010 Viola et al.
7,845,537 B2 12/2010 Shelton, IV et al.
7,857,185 B2 12/2010 Swayze et al.
7,870,989 B2 1/2011 Viola et al.
7,900,805 B2 3/2011 Shelton, IV et al.
7,905,897 B2 3/2011 Whitman et al.
7,918,230 B2 4/2011 Whitman et al.
7,922,061 B2 4/2011 Shelton, IV et al.
7,922,063 B2 4/2011 Racenet et al.
7,922,719 B2 4/2011 Ralph et al.
7,947,034 B2 5/2011 Whitman
7,951,071 B2 5/2011 Whitman et al.
7,954,682 B2 6/2011 Giordano et al.
7,959,051 B2 6/2011 Smith et al.
7,963,433 B2 6/2011 Whitman et al.
7,967,178 B2 6/2011 Scirica et al.
7,967,179 B2 6/2011 Olson et al.
7,992,758 B2 8/2011 Whitman et al.
8,011,550 B2 9/2011 Aranyi et al.
8,016,178 B2 9/2011 Olson et al.
8,016,855 B2 9/2011 Whitman et al.
8,016,858 B2 9/2011 Whitman
8,020,743 B2 9/2011 Shelton, IV
8,025,199 B2 9/2011 Whitman et al.
8,035,487 B2 10/2011 Malackowski
8,052,024 B2 11/2011 Viola et al.
8,114,118 B2 2/2012 Knodel et al.
8,127,975 B2 3/2012 Olson et al.
8,132,705 B2 3/2012 Viola et al.
8,152,516 B2 4/2012 Harvey et al.
8,157,150 B2 4/2012 Viola et al.
8,157,151 B2 4/2012 Ingmanson et al.
8,182,494 B1 5/2012 Yencho et al.
8,186,555 B2 5/2012 Shelton, IV et al.
8,186,587 B2 5/2012 Zmood et al.
8,220,367 B2 7/2012 Hsu
8,235,273 B2 8/2012 Olson et al.
8,241,322 B2 8/2012 Whitman et al.
8,246,637 B2 8/2012 Viola et al.
8,272,554 B2 9/2012 Whitman et al.
8,292,150 B2 10/2012 Bryant
8,292,888 B2 10/2012 Whitman
8,342,379 B2 1/2013 Whitman et al.
8,348,122 B2 * 1/2013 Milliman ............. A61B 17/115 227/175.1
8,348,130 B2 1/2013 Shah et al.
8,348,855 B2 1/2013 Hillely et al.
8,353,440 B2 1/2013 Whitman et al.
8,357,144 B2 1/2013 Whitman et al.
8,365,633 B2 2/2013 Simaan et al.
8,365,972 B2 2/2013 Aranyi et al.
8,371,492 B2 2/2013 Aranyi et al.
8,372,057 B2 2/2013 Cude et al.
8,391,957 B2 3/2013 Carlson et al.
8,403,926 B2 3/2013 Nobis et al.
8,418,904 B2 4/2013 Wenchell et al.
8,424,739 B2 4/2013 Racenet et al.
8,454,585 B2 6/2013 Whitman
8,460,275 B2 6/2013 Taylor et al.
8,505,802 B2 8/2013 Viola et al.
8,517,241 B2 8/2013 Nicholas et al.
8,523,043 B2 9/2013 Ullrich et al.
8,551,076 B2 10/2013 Duval et al.
8,561,871 B2 10/2013 Rajappa et al.
8,561,874 B2 10/2013 Scirica
8,590,763 B2 11/2013 Milliman
8,602,287 B2 12/2013 Yates et al.
8,623,000 B2 1/2014 Humayun et al.
8,627,995 B2 1/2014 Smith et al.
8,632,463 B2 1/2014 Drinan et al.
8,636,766 B2 1/2014 Milliman et al.
8,647,258 B2 2/2014 Aranyi et al.

(56) References Cited

U.S. PATENT DOCUMENTS 8,652,121 B2 2/2014 Quick et al.
8,657,174 B2 2/2014 Yates et al.
8,657,177 B2 2/2014 Scirica et al.
8,672,206 B2 3/2014 Aranyi et al.
8,696,552 B2 4/2014 Whitman
8,708,213 B2 4/2014 Shelton, IV et al.
8,715,306 B2 5/2014 Faller et al.
8,758,391 B2 6/2014 Swayze et al.
8,806,973 B2 8/2014 Ross et al.
8,808,311 B2 8/2014 Heinrich et al.
8,820,605 B2 9/2014 Shelton, IV
8,851,355 B2 10/2014 Aranyi et al.
8,858,571 B2 10/2014 Shelton, IV et al.
8,875,972 B2 11/2014 Weisenburgh et al.
8,888,762 B2 11/2014 Whitman
8,893,946 B2 11/2014 Boudreaux et al.
8,899,462 B2 12/2014 Kostrzewskii et al.
8,905,289 B2 12/2014 Patel et al.
8,919,630 B2 12/2014 Milliman
8,931,680 B2 1/2015 Milliman
8,939,344 B2 1/2015 Olson et al.
8,950,646 B2 2/2015 Viola
8,956,306 B2 2/2015 Hibner
8,960,519 B2 2/2015 Whitman et al.
8,961,396 B2 2/2015 Azarbarzin et al.
8,967,443 B2 3/2015 Mccuen
8,968,276 B2 3/2015 Zemlok et al.
8,968,337 B2 3/2015 Whitfield et al.
8,992,422 B2 3/2015 Spivey et al.
9,016,545 B2 4/2015 Aranyi et al.
9,023,014 B2 5/2015 Chowaniec et al.
9,033,868 B2 5/2015 Whitman et al.
9,055,943 B2 6/2015 Zemlok et al.
9,064,653 B2 6/2015 Prest et al.
9,072,515 B2 7/2015 Hall et al.
9,113,847 B2 8/2015 Whitman et al.
9,113,875 B2 8/2015 Viola et al.
9,113,876 B2 8/2015 Zemlok et al.
9,113,899 B2 8/2015 Garrison et al.
9,216,013 B2 12/2015 Scirica et al.
9,282,961 B2 3/2016 Whitman et al.
9,282,963 B2 3/2016 Bryant
9,295,522 B2 3/2016 Kostrzewskii
9,307,986 B2 4/2016 Hall et al.
RE46,135 E 9/2016 Hibner et al.
9,579,099 B2 2/2017 Penna et al.
9,955,966 B2* 5/2018 Zergiebel ......... A61B 17/07207
10,226,254 B2 3/2019 Cabrera et al.
10,463,365 B2 11/2019 Williams
10,561,417 B2 2/2020 Zergiebel et al.
10,729,443 B2 8/2020 Cabrera et al.
11,399,836 B2 8/2022 Cabrera et al.
11,547,394 B2* 1/2023 Zergiebel ................. H01H 9/20
2001/0031975 A1 10/2001 Whitman et al.
2002/0049454 A1 4/2002 Whitman et al.
2002/0165541 A1 11/2002 Whitman
2003/0038938 A1 2/2003 Jung et al.
2003/0165794 A1 9/2003 Matoba
2004/0111012 A1 6/2004 Whitman
2004/0133189 A1 7/2004 Sakurai
2004/0153124 A1 8/2004 Whitman
2004/0176751 A1 9/2004 Weitzner et al.
2004/0193146 A1 9/2004 Lee et al.
2005/0125027 A1 6/2005 Knodel et al.
2005/0131442 A1 6/2005 Yachia et al.
2005/0165328 A1 7/2005 Heske et al.
2006/0074407 A1 4/2006 Padget et al.
2006/0085033 A1 4/2006 Criscuolo et al.
2006/0142656 A1 6/2006 Malackowski et al.
2006/0142740 A1 6/2006 Sherman et al.
2006/0142744 A1 6/2006 Boutoussov
2006/0241692 A1 10/2006 Mcguckin et al.
2006/0259073 A1 11/2006 Miyamoto et al.
2006/0278680 A1 12/2006 Viola et al.
2006/0284730 A1 12/2006 Schmid et al.
2007/0023476 A1 2/2007 Whitman et al.
2007/0023477 A1 2/2007 Whitman et al.
2007/0029363 A1 2/2007 Popov
2007/0039996 A1* 2/2007 Mather ................ A61B 17/072
227/176.1
2007/0084897 A1 4/2007 Shelton, IV et al.
2007/0102472 A1 5/2007 Shelton, IV
2007/0114261 A1 5/2007 Ortiz et al.
2007/0152014 A1 7/2007 Gillum et al.
2007/0175947 A1 8/2007 Ortiz et al.
2007/0175949 A1 8/2007 Shelton, IV et al.
2007/0175950 A1 8/2007 Shelton, IV et al.
2007/0175951 A1 8/2007 Shelton, IV et al.
2007/0175955 A1 8/2007 Shelton, IV et al.
2007/0175961 A1 8/2007 Shelton, IV et al.
2007/0270784 A1 11/2007 Smith et al.
2008/0029570 A1 2/2008 Shelton, IV et al.
2008/0029573 A1 2/2008 Shelton, IV et al.
2008/0029574 A1 2/2008 Shelton, IV et al.
2008/0029575 A1 2/2008 Shelton, IV et al.
2008/0036206 A1 2/2008 Li-guo
2008/0058801 A1 3/2008 Taylor et al.
2008/0105730 A1 5/2008 Racenet et al.
2008/0109012 A1 5/2008 Falco et al.
2008/0110958 A1 5/2008 Mckenna et al.
2008/0147089 A1 6/2008 Loh et al.
2008/0167736 A1 7/2008 Swayze et al.
2008/0185419 A1 8/2008 Smith et al.
2008/0188841 A1 8/2008 Tomasello et al.
2008/0197167 A1 8/2008 Viola et al.
2008/0208195 A1 8/2008 Shores et al.
2008/0237296 A1 10/2008 Boudreaux et al.
2008/0251561 A1 10/2008 Eades et al.
2008/0255413 A1 10/2008 Zemlok et al.
2008/0255607 A1 10/2008 Zemlok
2008/0262654 A1 10/2008 Omori et al.
2008/0308603 A1 12/2008 Shelton, IV et al.
2009/0012533 A1 1/2009 Barbagli et al.
2009/0090763 A1 4/2009 Zemlok et al.
2009/0099876 A1 4/2009 Whitman
2009/0108048 A1 4/2009 Zemlok et al.
2009/0138006 A1 5/2009 Bales et al.
2009/0171147 A1 7/2009 Lee et al.
2009/0182193 A1 7/2009 Whitman et al.
2009/0209990 A1 8/2009 Yates et al.
2009/0250501 A1 10/2009 Sonnenschein et al.
2009/0254094 A1 10/2009 Knapp et al.
2009/0299141 A1 12/2009 Downey et al.
2010/0023022 A1 1/2010 Zeiner et al.
2010/0069942 A1 3/2010 Shelton, IV
2010/0076459 A1 3/2010 Farascioni
2010/0076461 A1 3/2010 Viola et al.
2010/0193568 A1 8/2010 Scheib et al.
2010/0211053 A1 8/2010 Ross et al.
2010/0225073 A1 9/2010 Porter et al.
2010/0280605 A1* 11/2010 Hammer ............... A61F 2/2436
623/2.11
2010/0320252 A1 12/2010 Viola et al.
2011/0071508 A1 3/2011 Duval et al.
2011/0077673 A1 3/2011 Grubac et al.
2011/0121049 A1 5/2011 Malinouskas et al.
2011/0125138 A1 5/2011 Malinouskas et al.
2011/0139851 A1 6/2011 Mccuen
2011/0155783 A1 6/2011 Rajappa et al.
2011/0155786 A1 6/2011 Shelton, IV
2011/0172648 A1 7/2011 Jeong
2011/0174099 A1 7/2011 Ross et al.
2011/0184245 A1 7/2011 Xia et al.
2011/0186614 A1* 8/2011 Kasvikis .......... A61B 17/07207
227/176.1
2011/0204119 A1 8/2011 Mccuen
2011/0218522 A1 9/2011 Whitman
2011/0276057 A1 11/2011 Conlon et al.
2011/0290854 A1 12/2011 Timm et al.
2011/0295242 A1 12/2011 Spivey et al.
2011/0295269 A1 12/2011 Swensgard et al.
2012/0000962 A1 1/2012 Racenet et al.
2012/0074199 A1 3/2012 Olson et al.
2012/0089131 A1 4/2012 Zemlok et al.

(56) References Cited

U.S. PATENT DOCUMENTS

2012/0104071 A1 5/2012 Bryant
2012/0116368 A1 5/2012 Viola
2012/0143002 A1 6/2012 Aranyi et al.
2012/0172924 A1 7/2012 Allen, IV
2012/0203247 A1* 8/2012 Shelton, IV ......... A61B 17/072 227/176.1
2012/0211542 A1 8/2012 Racenet
2012/0211546 A1* 8/2012 Shelton, IV ..... A61B 17/07207 227/177.1
2012/0223121 A1 9/2012 Viola et al.
2012/0245428 A1 9/2012 Smith et al.
2012/0253329 A1 10/2012 Zemlok et al.
2012/0298719 A1 11/2012 Shelton et al.
2012/0310220 A1 12/2012 Malkowski et al.
2012/0323226 A1 12/2012 Chowaniec et al.
2012/0330285 A1 12/2012 Hartoumbekis et al.
2013/0018361 A1 1/2013 Bryant
2013/0093149 A1 4/2013 Saur et al.
2013/0098966 A1 4/2013 Kostrzewskii et al.
2013/0181029 A1 7/2013 Milliman
2013/0181035 A1 7/2013 Milliman
2013/0184704 A1 7/2013 Beardsley et al.
2013/0214025 A1 8/2013 Zemlok et al.
2013/0274722 A1 10/2013 Kostrzewskii et al.
2013/0282052 A1 10/2013 Aranyi et al.
2013/0292451 A1 11/2013 Viola et al.
2013/0313304 A1 11/2013 Shelton, IV et al.
2013/0317486 A1 11/2013 Nicholas et al.
2013/0319706 A1 12/2013 Nicholas et al.
2013/0324978 A1 12/2013 Nicholas et al.
2013/0324979 A1 12/2013 Nicholas et al.
2013/0334281 A1 12/2013 Williams
2014/0005677 A1 1/2014 Shelton, IV et al.
2014/0012236 A1 1/2014 Williams et al.
2014/0012237 A1 1/2014 Pribanic et al.
2014/0012289 A1 1/2014 Snow et al.
2014/0025046 A1 1/2014 Williams et al.
2014/0110455 A1 4/2014 Ingmanson et al.
2014/0114334 A1 4/2014 Olson et al.
2014/0138423 A1 5/2014 Whitfield et al.
2014/0207125 A1 7/2014 Applegate et al.
2014/0207182 A1 7/2014 Zergiebel et al.
2014/0207185 A1 7/2014 Goble et al.
2014/0236173 A1 8/2014 Scirica et al.
2014/0236174 A1 8/2014 Williams et al.
2014/0257033 A1 9/2014 Frering
2014/0263539 A1* 9/2014 Leimbach .............. G16H 20/40 227/175.1
2014/0263544 A1* 9/2014 Ranucci ................ A61F 2/0063 227/175.2
2014/0276776 A1 9/2014 Parihar et al.
2014/0276932 A1 9/2014 Williams et al.
2014/0299647 A1 10/2014 Scirica et al.
2014/0303668 A1 10/2014 Nicholas et al.
2014/0305992 A1 10/2014 Kimsey et al.
2014/0305993 A1* 10/2014 Timm .................... A61B 17/32 227/178.1
2014/0358129 A1 12/2014 Zergiebel et al.
2014/0361068 A1 12/2014 Aranyi et al.
2014/0365235 A1 12/2014 Deboer et al.
2014/0373652 A1 12/2014 Zergiebel et al.
2015/0014392 A1 1/2015 Williams et al.
2015/0048144 A1 2/2015 Whitman
2015/0053741 A1* 2/2015 Shelton, IV ........... A61B 90/03 227/175.3
2015/0060516 A1 3/2015 Collings et al.
2015/0076205 A1 3/2015 Zergiebel
2015/0080912 A1 3/2015 Sapre
2015/0108201 A1 4/2015 Williams
2015/0112381 A1 4/2015 Richard
2015/0122870 A1 5/2015 Zemlok et al.
2015/0133224 A1 5/2015 Whitman et al.
2015/0133957 A1 5/2015 Kostrzewskii
2015/0150547 A1 6/2015 Ingmanson et al.
2015/0150574 A1 6/2015 Richard et al.
2015/0157320 A1 6/2015 Zergiebel et al.
2015/0157321 A1 6/2015 Zergiebel et al.
2015/0164502 A1 6/2015 Richard et al.
2015/0190133 A1 7/2015 Penna et al.
2015/0201931 A1 7/2015 Zergiebel et al.
2015/0272577 A1 10/2015 Zemlok et al.
2015/0280384 A1* 10/2015 Leimbach ........ A61B 17/07207 227/175.1
2015/0297199 A1 10/2015 Nicholas et al.
2015/0303996 A1 10/2015 Calderoni
2015/0320420 A1 11/2015 Penna et al.
2015/0327850 A1 11/2015 Kostrzewskii
2015/0342601 A1 12/2015 Williams et al.
2015/0342603 A1 12/2015 Zergiebel et al.
2015/0351769 A1* 12/2015 Lee .................... A61B 17/1155 227/179.1
2015/0374366 A1 12/2015 Zergiebel et al.
2015/0374370 A1 12/2015 Zergiebel et al.
2015/0374371 A1 12/2015 Richard et al.
2015/0374372 A1 12/2015 Zergiebel et al.
2015/0374449 A1 12/2015 Chowaniec et al.
2015/0380187 A1 12/2015 Zergiebel et al.
2016/0095585 A1 4/2016 Zergiebel et al.
2016/0095596 A1 4/2016 Scirica et al.
2016/0106406 A1 4/2016 Cabrera et al.
2016/0113648 A1 4/2016 Zergiebel et al.
2016/0113649 A1 4/2016 Zergiebel et al.
2016/0199084 A1* 7/2016 Takei ................... A61B 17/295 606/170
2016/0296234 A1 10/2016 Richard et al.
2016/0338481 A1* 11/2016 Lee ........................ A61C 15/00
2016/0361057 A1 12/2016 Williams
2016/0374667 A1 12/2016 Miller et al.
2017/0086879 A1 3/2017 Williams
2017/0128123 A1* 5/2017 Williams ........... A61B 17/1155
2017/0196566 A1 7/2017 Sgroi
2018/0178366 A1 6/2018 Matei
2019/0090873 A1 3/2019 Fox et al.
2019/0125458 A1* 5/2019 Shelton, IV ............. A61B 5/00
2019/0290265 A1* 9/2019 Shelton, IV ........... G16H 40/63
2020/0222050 A1 7/2020 Eisinger
2020/0405304 A1 12/2020 Mozdzierz et al.
2021/0000472 A1 1/2021 Sgroi et al.
2021/0275169 A1* 9/2021 Xu ..................... A61B 17/0686
2022/0167973 A1* 6/2022 Shelton, IV ......... A61B 17/072
2022/0249182 A1* 8/2022 Definis .................. A61B 17/29
2022/0361883 A1 11/2022 Cabrera et al.
2024/0335196 A1* 10/2024 Abramek ......... A61B 17/07207

FOREIGN PATENT DOCUMENTS

CN 102247182 A 11/2011
CN 102551840 A 7/2012
CN 103717147 A 4/2014
DE 102008053842 A1 5/2010
EP 0705571 A1 4/1996
EP 1769754 A1 4/2007
EP 2055243 A2 5/2009
EP 2316345 A1 5/2011
EP 2333509 A1 6/2011
EP 2668910 A2 12/2013
EP 2684530 A1 * 1/2014 ........... A61B 17/068
EP 2883504 A2 6/2015
EP 3508161 B1 3/2023
ES 2333509 A1 2/2010
JP H067357 A 1/1994
JP H0838488 A 2/1996
JP H08182684 A 7/1996
JP 2005125075 A 5/2005
JP 2011115594 A 6/2011
JP 2013248395 A 12/2013
JP 2016077905 A 5/2016
JP 2019213964 A 12/2019
KR 20120022521 A 3/2012
WO 2006026520 A2 3/2006
WO 2008045333 A2 4/2008
WO 2011108840 A2 9/2011

(56) References Cited

FOREIGN PATENT DOCUMENTS

| | | |
|---|---|---|
| WO | 2012040984 A1 | 4/2012 |
| WO | 2012166499 A1 | 12/2012 |
| WO | 2015041845 A2 | 3/2015 |

OTHER PUBLICATIONS

Examination Report received for Australian Patent Application No. 2015200153, mailed on Dec. 11, 2015, 3 pages.
Examination Report received for Australian Patent Application No. 2015243004, mailed on Jul. 23, 2019, 3 pages.
Extended European Search Report received for European Patent Application No. 12197970.2, mailed on Jan. 28, 2016, 7 pages.
Extended European Search Report received for European Patent Application No. 14196704.2, mailed on Sep. 24, 2015, 11 pages.
Extended European Search Report received for European Patent Application No. 14197563.1, mailed on Aug. 5, 2015, 13 pages.
Extended European Search Report received for European Patent Application No. 14199783.3, mailed on Dec. 22, 2015, 14 pages.
Extended European Search Report received for European Patent Application No. 15151076.5, mailed on Apr. 22, 2015, 7 pages.
Extended European Search Report received for European Patent Application No. 15166899.3, mailed on Feb. 3, 2016, 9 pages.
Extended European Search Report received for European Patent Application No. 15167793.7, mailed on Apr. 5, 2016, 12 pages.
Extended European Search Report received for European Patent Application No. 15173803.6, mailed on Nov. 24, 2015, 6 pages.
Extended European Search Report received for European Patent Application No. 15173804.4, mailed on Nov. 24, 2015, 6 pages.
Extended European Search Report received for European Patent Application No. 15173807.7, mailed on Nov. 24, 2015, 6 pages.
Extended European Search Report received for European Patent Application No. 15173910.9, mailed on Nov. 13, 2015, 6 pages.
Extended European Search Report received for European Patent Application No. 15184915.5, mailed on Jan. 5, 2016, 7 pages.
Extended European Search Report received for European Patent Application No. 15188539.9, mailed on Feb. 17, 2016, 9 pages.
Extended European Search Report received for European Patent Application No. 15190245.9, mailed on Jan. 28, 2016, 11 pages.
Extended European Search Report received for European Patent Application No. 15190760.7, mailed on Apr. 1, 2016, 7 pages.
Extended European Search Report received for European Patent Application No. 19191409.2, mailed on Dec. 13, 2019, 9 pages.
Extended European Search Report received for European Patent Application No. 19192171.7, mailed on Dec. 6, 2019, 12 pages.
International Search Report and Written Opinion received for PCT Application No. PCT/US2015/051837, mailed on Dec. 21, 2015, 10 pages.
Non-Final Office Action received for U.S. Appl. No. 16/262,242, mailed on Nov. 17, 2020, 10 pages.
Non-Final Office Action received for U.S. Appl. No. 17/878,131, mailed on Jul. 19, 2024, 10 pages.
Non-Final Office Action received for U.S. Appl. No. 17/878,131, mailed on Sep. 21, 2023, 16 pages.
Office Action received for Chinese Patent Application No. 201210560638.1, mailed on Oct. 21, 2015.
Office Action received for Chinese Patent Application No. 201310125449.6, mailed on Feb. 3, 2016.
Office Action received for Chinese Patent Application No. 201510843610.2, mailed on Dec. 12, 2018.
Office Action received for Chinese Patent Application No. 201510843610.2, mailed on Sep. 4, 2019.
Office Action received for Chinese Patent Application No. 202010402058.4, mailed on Dec. 28, 2022.
Office Action received for European Patent Application No. 14152236.7, mailed on Aug. 11, 2015, 5 pages.
Office Action received for European Patent Application No. 14159056.2, mailed on Oct. 26, 2015, 4 pages.
Office Action received for European patent Application No. 14184882.0, mailed on Apr. 25, 2016, 4 pages.
Office Action received for Japanese Patent Application No. 2011-084092, mailed on Jan. 14, 2016.
Office Action received for Japanese Patent Application No. 2015-206306, issued on May 28, 2019.
Office Action received for Japanese Patent Application No. 2019-175306, mailed on Jun. 24, 2021, 8 pages (English Translation).
Office Action received for Japanese Patent Application No. 2019-175306, mailed on Oct. 23, 2020, 10 pages (English Translation).
Office Action received for Japanese Patent Application No. 2021-173766, mailed on Mar. 16, 2023.
Partial European Search Report received for European Patent Application No. 15190643.5, mailed on Feb. 26, 2016, 7 pages.

* cited by examiner

114
LOAD
124a
118
116
122a
113
120
126a
144b
142b
144a
146b
142a
146a
140
145

114
113
126a
122a
116
120
124a
118
140
138
166a
166
166b
160
10

186a
186
186b
180
16

150
164
192a
192b
194a
196
194b
185
180
188a
188
186a
108
188b
190
184
"B"
"B"

150
192a
194a
196
180
185
182
194b
194b
188
184
108
190
198
198
"B"
"B"

186a
192a
150
194a
186b
194b
188b
194a
186
188
194b
192b
188b 32
208a
208
241
243
240
242
221
222
220
202
223
26
26
206
200
25
25
290
32

300
"A"
304
302
41
41
364a
360a
312
312a
314
307
307a
360c
360b
364b
360g
360f
360e
360d
310
320

304
300
302
310
320

ADAPTER, EXTENSION, AND CONNECTOR ASSEMBLIES FOR SURGICAL DEVICES

CROSS-REFERENCE TO RELATED APPLICATIONS

This application is a continuation of U.S. application Ser. No. 17/878,131 filed Aug. 1, 2022, now U.S. Pat. No. 12,262,893, which is a continuation application of U.S. application Ser. No. 16/262,242 filed Jan. 30, 2019, now U.S. Pat. No. 11,399,836, which is a divisional of U.S. application Ser. No. 14/875,766 filed Oct. 6, 2015, now U.S. Pat. No. 10,226,254, which claims the benefit of and priority to U.S. Provisional Patent Application No. 62/066,518 filed Oct. 21, 2014, the entire disclosures each of which are incorporated by reference herein.

FIELD

The present disclosure relates generally to powered surgical devices. More specifically, the present disclosure relates to adapter and extension assemblies for selectively connecting end effectors to the actuation units of the powered surgical devices.

BACKGROUND

Powered devices for use in surgical procedures are known. To permit reuse of the handle assemblies of these powered surgical devices and so that the handle assembly may be used with a variety of end effectors, adapter assemblies and extension assemblies have been developed for selective attachment to the handle assemblies and to a variety of end effectors. Following use, the adapter and/or extension assemblies may be disposed of along with the end effector. In some instances, the adapter assemblies and extension assemblies may be sterilized for reuse.

SUMMARY

An assembly for operably connecting an end effector to an electrosurgical instrument is provided. The assembly includes an adapter assembly and an extension assembly. The adapter assembly includes a connector assembly, a drive transfer assembly operably received through the connector assembly and including first, second, and third rotatable shafts, a first pusher assembly operably connected to the first rotatable shaft for converting rotational motion from the first rotatable shaft to longitudinal movement to perform a first function, a second pusher assembly operably connected to the second rotatable shaft for converting rotational motion from the second rotatable shaft to longitudinal movement to perform a second function, and a drive member operably connected to the third rotatable shaft for transferring rotational motion from the third rotatable shaft to perform a third function. The drive transfer assembly and the first and second pusher assemblies are operably received within a single outer tube. The extension is operably connected to a distal end of the adapter assembly and includes at least one flexible band assembly operably connected to one of the first and second pusher assemblies.

In embodiments, the first pusher assembly includes a first planetary gear assembly and the second pusher assembly includes a second planetary gear assembly. Each of the first and second planetary gear assemblies may include a first planetary gear system and a second planetary gear system. Each of the first and second planetary gear systems may be configured to reduce a speed of rotation of the first and second rotatable shafts. The first pusher assembly may include a first drive screw operably connected to the first planetary gear assembly and the second pusher assembly may include a second drive screw operably connected to the second planetary gear assembly. The first pusher assembly may include a first pusher member operably received about the first drive screw and the second pusher assembly may include a second pusher member operably received about the second screw member. Rotation of the first drive screw may cause longitudinal movement of the first pusher member and rotation of the second drive screw may cause longitudinal movement of the second pusher member. The adapter assembly may further include a base and a support structure rotatable relative to the base along a longitudinal axis, the connector assembly and the drive transfer assembly being disposed with in the base and the first and second pusher assemblies being disposed within the support structure. The connection assembly may be configured for operable connection to an electrosurgical instrument.

In some embodiments, the extension assembly includes a second flexible band assembly operably connected to the other of the first and second pusher assemblies. The extension assembly may include a trocar assembly operably connected to the drive member. The trocar assembly may convert rotational motion from the drive member into linear motion. The extension assembly may include a link assembly operably connecting the trocar assembly to the drive member. The link assembly may include a first drive shaft pivotally connected to a second drive shaft and a coupling member pivotally connected to the second drive shaft.

An extension assembly for operably connecting an end effector to an electrosurgical instrument is also provided. The extension assembly includes an outer sleeve, a frame assembly received within the outer sleeve, an inner flexible band assembly slidably disposed within the frame assembly for performing a first function, an outer flexible band assembly slidably disposed within the frame assembly and relative to the inner flexible band assembly for performing a second function, and a trocar assembly disposed within the frame assembly and including a trocar member for performing a third function. The inner flexible band assembly may include a proximal end configured for connection to a first linear drive member and the outer flexible band assembly may include a proximal end configured for connection to a second linear drive member. A proximal end of the trocar assembly may be configured for connection to a rotatable drive shaft. Rotation of the rotatable drive shaft may cause linear advancement of the trocar member. The extension assembly may further include a connection assembly configured for operable connection with an end effector. A distal end of the inner flexible band assembly may include a flange configured for operable connection with an end effector and a distal end of the outer flexible band assembly includes a flange configured for operable connection with an end effector. The trocar member may be configured for operably connection with an anvil assembly. The extension assembly may further include a link assembly for operable connection with the trocar assembly, the link assembly including a first shaft pivotally secured to a second shaft and a coupling member.

Also provided is a connection assembly for securing a first tubular member to a second tubular member. The connection assembly includes a tubular base having a flange and an annular rim. The connection assembly further includes a tubular extension having first and second sections and an outer sleeve slidably disposed about the first and second sections. The first and second sections may define an annular groove positioned to receive the annular rim of the tubular base when the first and second sections are received about the flange. The tubular base may be secured to the first tubular member and the tubular extension may be secured to the second tubular member. The tubular base may be formed on an end of the first tubular member and the tubular extension is formed on an end of the second tubular member.

BRIEF DESCRIPTION OF THE DRAWINGS

Embodiments of the present disclosure are described herein with reference to the accompanying drawings, wherein.

DETAILED DESCRIPTION

Figure 1:
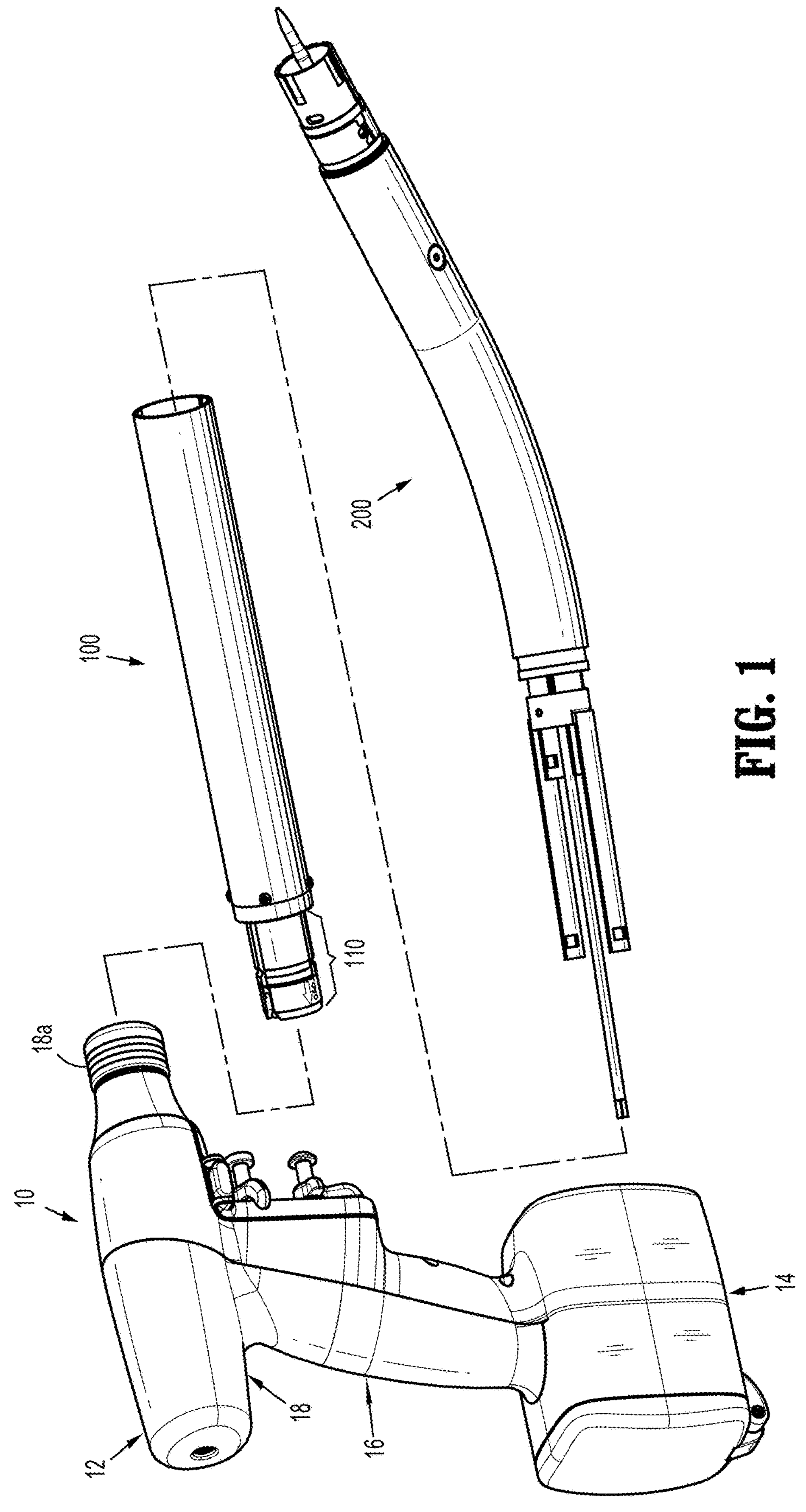
FIG. 1 is a perspective separated view of an adapter assembly, in accordance with an embodiment of the present disclosure, an extension assembly, in accordance with an embodiment of the present disclosure, and an exemplary electromechanical surgical device.

Embodiments of the presently disclosed adapter assemblies and extension assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, an adapter assembly in accordance with an embodiment of the present disclosure, shown generally as adapter assembly 100, and an extension assembly according to an embodiment of the present disclosure, shown generally as extension assembly 200, are configured for selective connection to a powered hand held electromechanical instrument shown, generally as surgical device 10. As illustrated in FIG. 1, surgical device 10 is configured for selective connection with adapter assembly 100, and, in turn, adapter assembly 100 is configured for selective connection with an extension assembly 200. Extension assembly 200 is configured for selective connection with a tool assembly or end effector, e.g. tool assembly 30 (FIG. 34), including a loading unit, e.g. loading unit 40 (FIG. 34), and an anvil assembly, e.g., anvil assembly 50 (FIG. 34), for applying a circular array of staples (not shown) to tissue (not shown).

Figure 2:
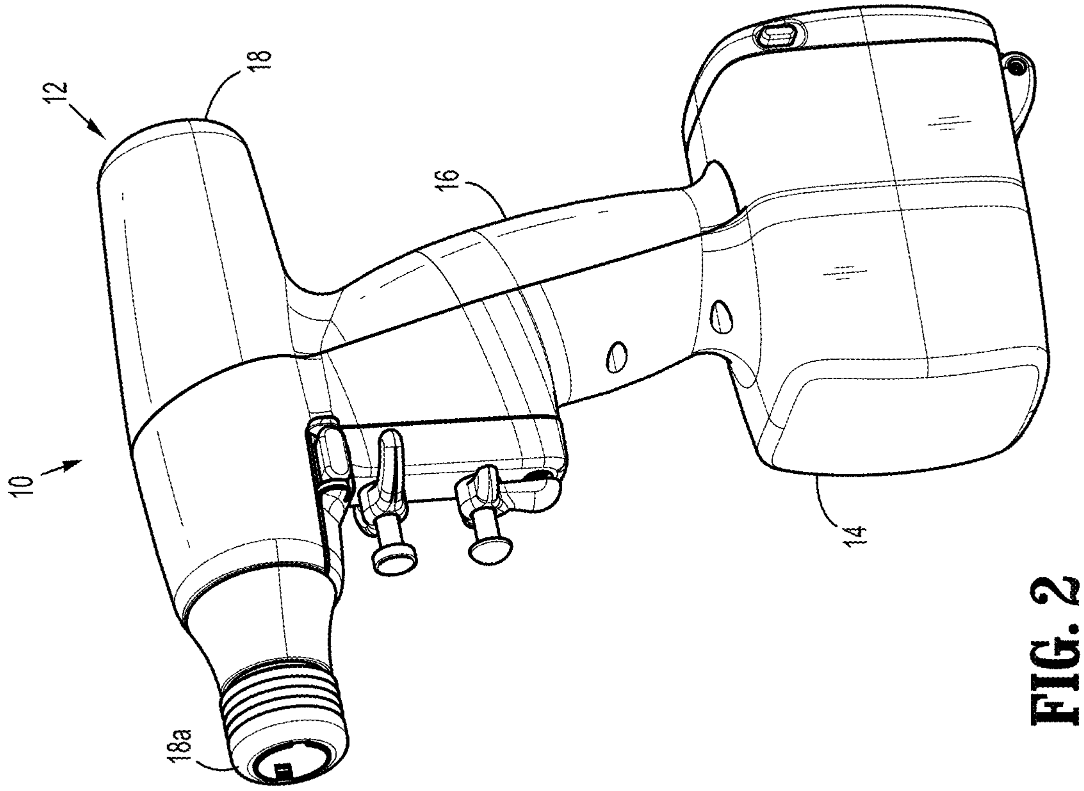
FIG. 2 is a perspective side view of the exemplary electromechanical surgical device of FIG. 1.

As illustrated in FIGS. 1 and 2, surgical device 10 includes a handle housing 12 having a lower housing portion 14, an intermediate housing portion 16 extending from and/or supported on lower housing portion 14, and an upper housing portion 18 extending from and/or supported on intermediate housing portion 16. A distal half-section of upper housing portion 18 defines a nose or connecting portion 18*a* configured to accept a corresponding drive coupling assembly 110 (FIG. 10) of adapter assembly 100. For a detailed description of the structure and function of an exemplary electromechanical instrument, please refer to commonly owned U.S. Pat. Appl. Publ. No. 2012/0253329 ("the '329 application"), the contents of which is incorporated by reference herein in its entirety.

Figures 3, 4, 5:
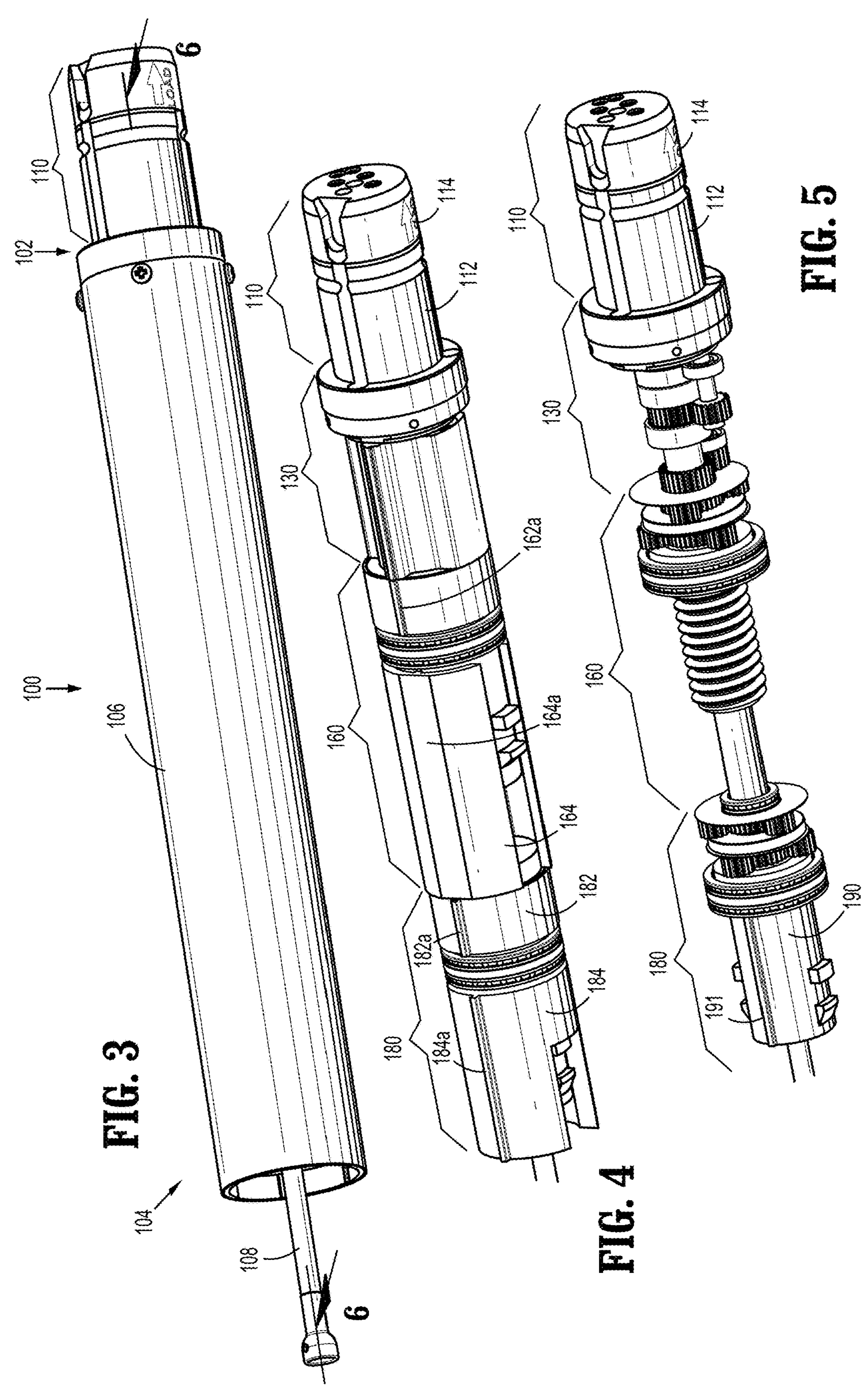
FIG. 3 is a perspective side view of the adapter assembly of FIG. 1.
FIG. 4 is a perspective side view of the adapter assembly of FIG. 3 with the outer sleeve removed.
FIG. 5 is a perspective side view of the adapter assembly of FIGS. 3 and 4 with proximal and distal housings of first and second pusher assemblies removed.
Figures 6, 7:
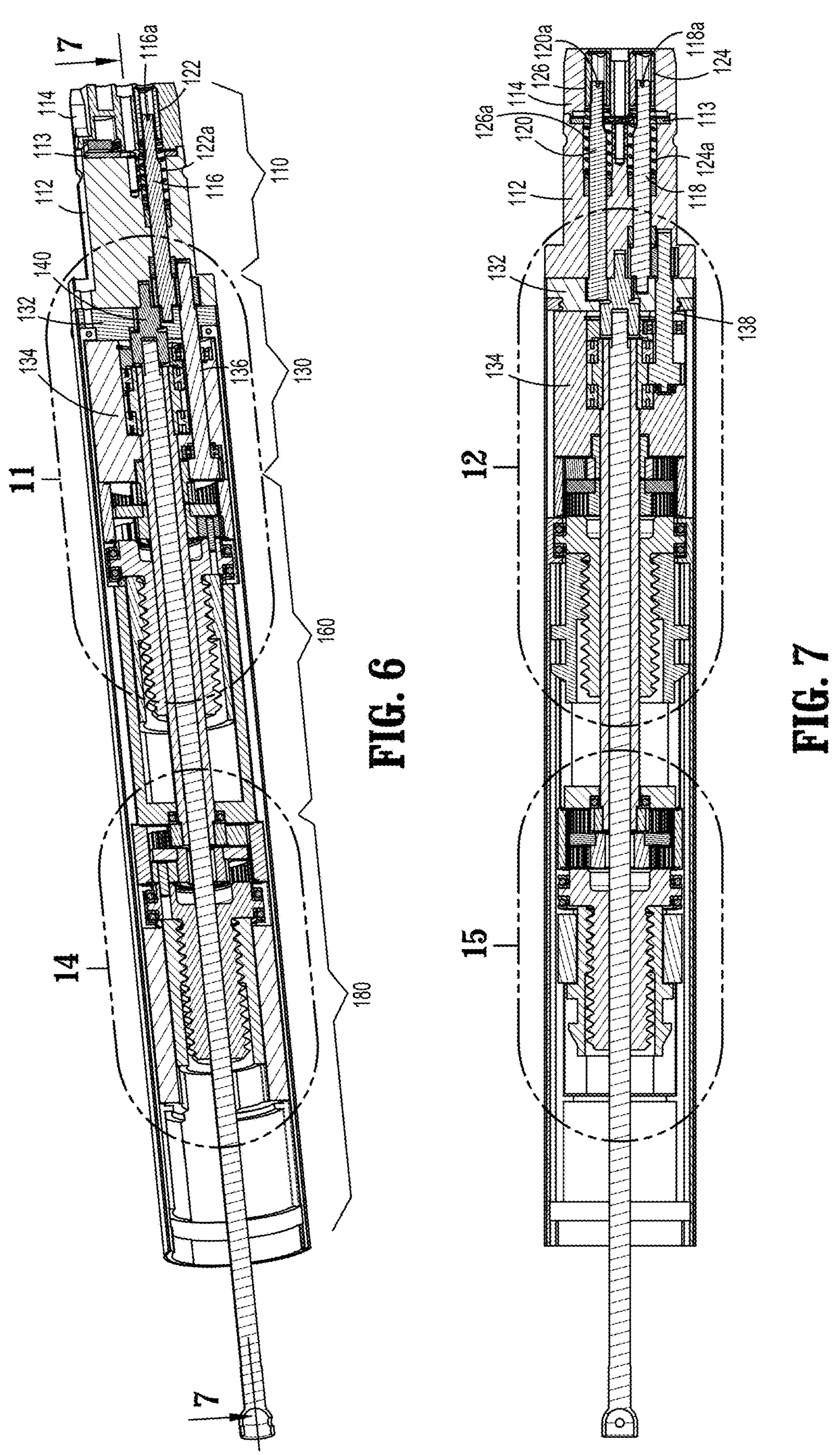
FIG. 6 is a cross-sectional side view of the adapter assembly of FIGS. 2-4 taken along line 6-6 in FIG. 3.
FIG. 7 is a cross-sectional side view of the adapter assembly of FIGS. 2-5 taken along line 7-7 in FIG. 5.
Figures 8, 9:
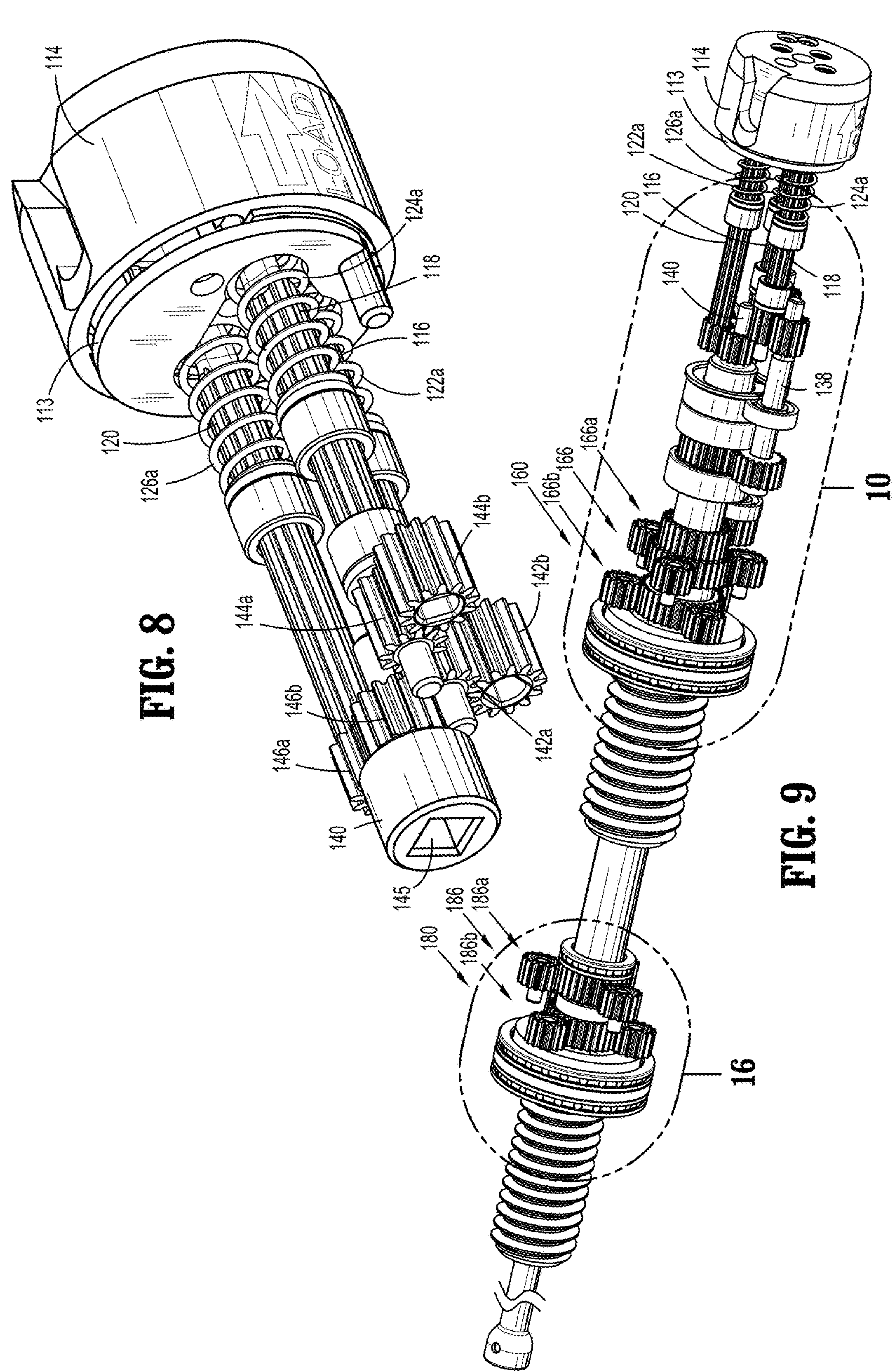
FIG. 8 is an enlarged, perspective view of a coupling assembly and a transfer assembly of the adapter assembly of FIGS. 2-7.
FIG. 9 is a perspective side view of adapter assembly of FIGS. 2-7 with the housing assemblies removed.

Adapter assembly 100 will now be described with reference to FIGS. 3-20. Referring initially to FIG. 3, adapter assembly 100 includes a proximal end 102 configured for operable connection to connecting portion 18*a* (FIG. 1) of surgical device 10 (FIG. 1) and a distal end 104 configured for operable connection to extension assembly 200 (FIG. 1).

Turning to FIGS. 3-5, from proximal end 102 to distal end 104 of adapter assembly 100 includes a drive coupling assembly 110, a drive transfer assembly 130 operably connected to drive coupling assembly 110, a first pusher assembly 160 operably connected to drive transfer assembly 130, and a second pusher assembly 180 operably connected to drive transfer assembly 130. Each of drive transfer assembly 130, first pusher assembly 160 and second pusher assembly 180 are operably maintained within an outer sleeve 106 (FIG. 3). As will be described in further detail below, a shaft 108 (FIG. 3) extends longitudinally through adapter assembly 100 and is operably connected to drive transfer assembly 130.

With reference to FIGS. 5-9, drive coupling assembly 110 has a cylindrical profile and is configured to selectively secure adapter assembly 100 to surgical device 10 (FIG. 1). Drive coupling assembly 110 includes a connector housing 112 and a connector extension 114 fixedly connected to connector housing 112 by a mounting plate 113. Connector housing 112 and connector extension 114 operate to rotatably support a first rotatable proximal drive shaft 116, a second rotatable proximal drive shaft 118, and a third rotatable proximal drive shaft 120. Connector housing 112 and connector extension 114 of drive coupling assembly 110 also rotatably support first, second, and third connector sleeves 122, 124, and 126, respectively. Each connector sleeve 122, 124, 126 is configured to mate with a respective first, second, or third drive connector (not shown) of surgical device 10 (FIG. 1). Each connector sleeve 122, 124, 126 is further configured to mate with a proximal end 116*a*, 118*a*, 120*a* of a respective first, second, or third rotatable proximal drive shaft 116, 118, 120.

Drive coupling assembly 110 also includes first, second and third biasing members 122a, 124a and 126a disposed distally of respective first, second and third connector sleeves 122, 124, 126. Each biasing member 122*a*, 124*a* and 126*a* is disposed about a respective first, second, or third rotatable proximal drive shafts 116, 118 and 120 to help maintain the corresponding connector sleeve 122, 124, 126 engaged with a respective drive connector (not shown) of surgical device 10 when adapter assembly 100 is connected to surgical device 10. In particular, first, second and third biasing members 122*a*, 124*a* and 126*a* function to bias respective connector sleeves 122, 124 and 126 in a proximal direction.

For a detailed description of an exemplary drive coupling assembly, please refer to the '329 application, the contents of which was previously incorporated by reference herein.

With reference to FIGS. 9-13, drive transfer assembly 130 has a cylindrical profile and operably connects distal ends of first, second and third rotatable proximal drive shafts 116, 118 and 120 to shaft 108, first pusher assembly 160, and second pusher assembly 180, respectively. Drive transfer assembly 130 includes a support plate 132 (FIGS. 11 and 12) secured to a proximal end of connector housing 112 and a drive transfer housing 134 positioned adjacent support plate 132. Support plate 132 and housing 134 operate to rotatably support a first rotatable distal drive shaft 136, a second rotatable distal drive shaft 138 and a drive member 140.

First and second rotatable distal drive shafts 136 and 138 are each operably connected to respective first and second rotatable proximal drive shafts 116 and 118 of drive coupling assembly 110 by a pair of gears. In particular, distal ends of each of first and second rotatable proximal drive shaft 116 and 118 include a geared portion 142*a* and 144*a*, respectively, which engages a proximal drive gear 142*b* and 144*b* on a proximal end of respective first and second distal drive shafts 136 and 138. As shown, each of respective paired geared portion and proximal drive gear 142*a*, 142*b* and 144*a*, 144*b* are the same size to provide a 1:1 gear ratio between the respective rotatable proximal and distal drive shafts. In this manner, respective rotatable proximal and distal drive shafts rotate at the same speed. However, it is envisioned that either or both of the paired geared portions and proximal drive gears may be of different sizes to alter the gear ratio between the rotatable proximal and distal drive shafts.

Figures 16, 17:
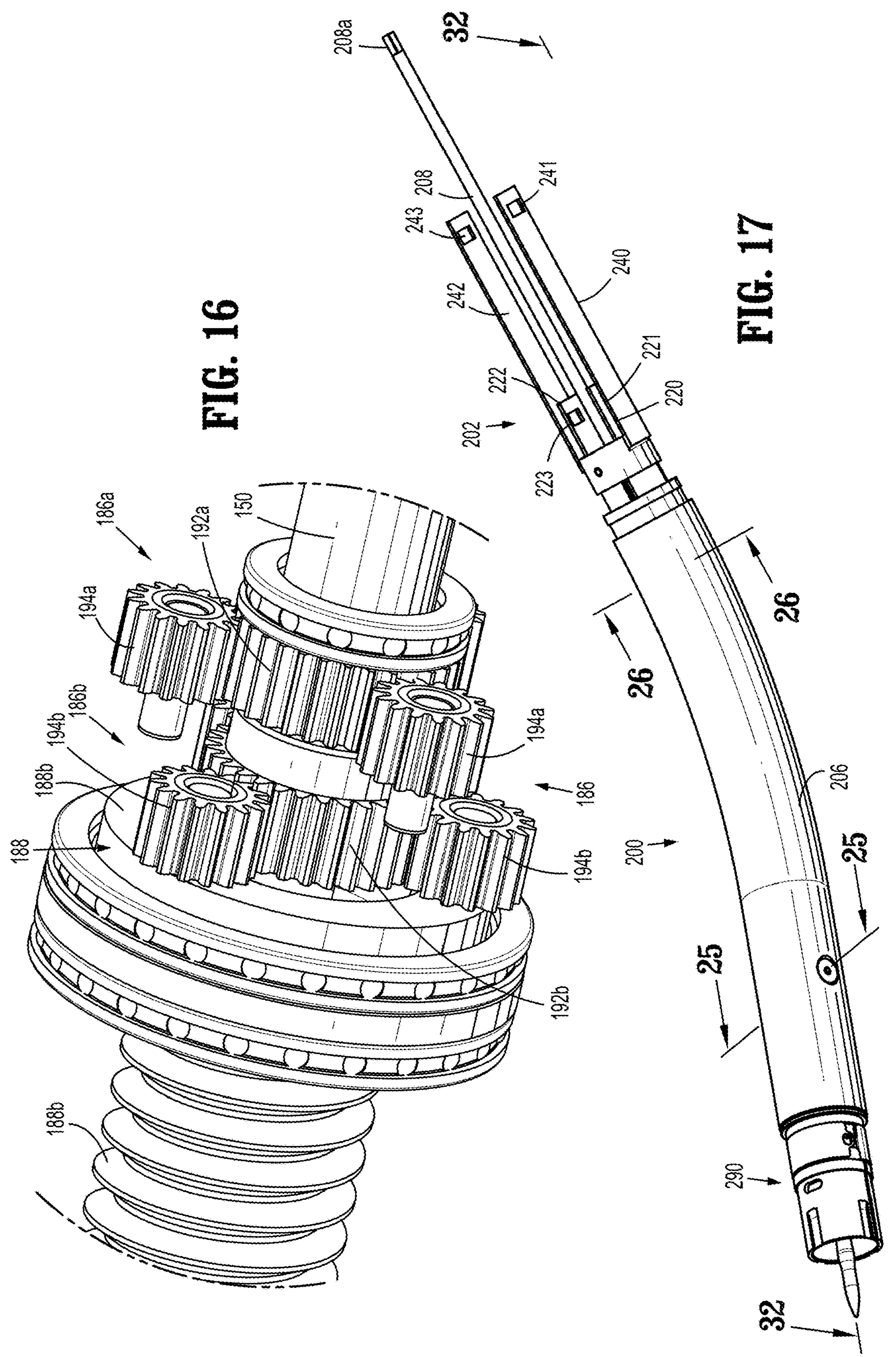
FIG. 16 is an enlarged view of the indicated area of detail of FIG. 9.
FIG. 17 perspective side view of the extension assembly of FIG. 1.

A distal end of third proximal drive shaft 120 of drive coupling assembly 110 includes a geared portion 146*a* that engages a geared portion 146*b* formed on a proximal end of drive member 140 of drive transfer assembly 130. The size of geared portion 146*a* on third proximal drive shaft 120 and geared portion **146*b* on drive member 140 are the same size to provide a 1:1 gear ratio between third proximal drive shaft 120 and drive member 140. In this manner, third proximal drive shaft 120 and drive member 140 rotate at the same speed. However, it is envisioned that either or both of geared portions 146*a*, 146*b* may be of different sizes to alter the gear ratio between third proximal drive shaft 120 and drive member 140. A distal end of drive member 140 defines a socket 145 that receives a proximal end 108*a* of shaft 108. Alternatively, socket 145 may be configured to operably engage a proximal end 208*a* of a drive shaft (FIG. 17) of an extension assembly 200 (FIG. 17**).

Drive transfer assembly 130 also includes a drive connector 148 (FIG. 11) operably connecting first rotatable distal drive shaft 136 to first pusher assembly 160 and a tubular connector 150 operably connecting second rotatable distal drive shaft 138 to second pusher assembly 180. In particular, a distal end of first rotatable distal drive shaft 136 includes a geared portion **152*a* that engages a geared portion 152*b* of drive connector 148. A distal end of second rotatable distal drive shaft 138 includes a geared portion 154*a* that engages a drive gear 154*b* secured to a distal end of tubular connector 150**.

As shown, geared portion **152*a* of first rotatable distal drive shaft 136 is smaller than geared portion 152*b* of drive connector 148 to provide a gear ratio of greater than 1:1 between first rotatable distal drive shaft 136 and drive connector 148. In this manner, drive connector 148 rotates at a slower speed than first rotatable distal drive shaft 136. Similarly, geared portion 154*a* of second rotatable distal drive shaft 138 is smaller than drive gear 154*b* on tubular connector 150 to provide a gear ratio of greater than 1:1 between second rotatable distal drive shaft 138 and drive connector 148. In this manner, tubular connector 150 rotates at a slower speed than second rotatable distal drive shaft 138. However, it is envisioned that each of paired geared portion 152*a* and geared portion 152*b*, and geared portion 154*a* and drive gear 154*b* may be the same size to provide a gear ratio of 1:1 between respective first rotatable distal drive shaft 136 and drive connector 148 and between second rotatable distal drive shaft 138 and tubular connector 150**.

Figure 10:
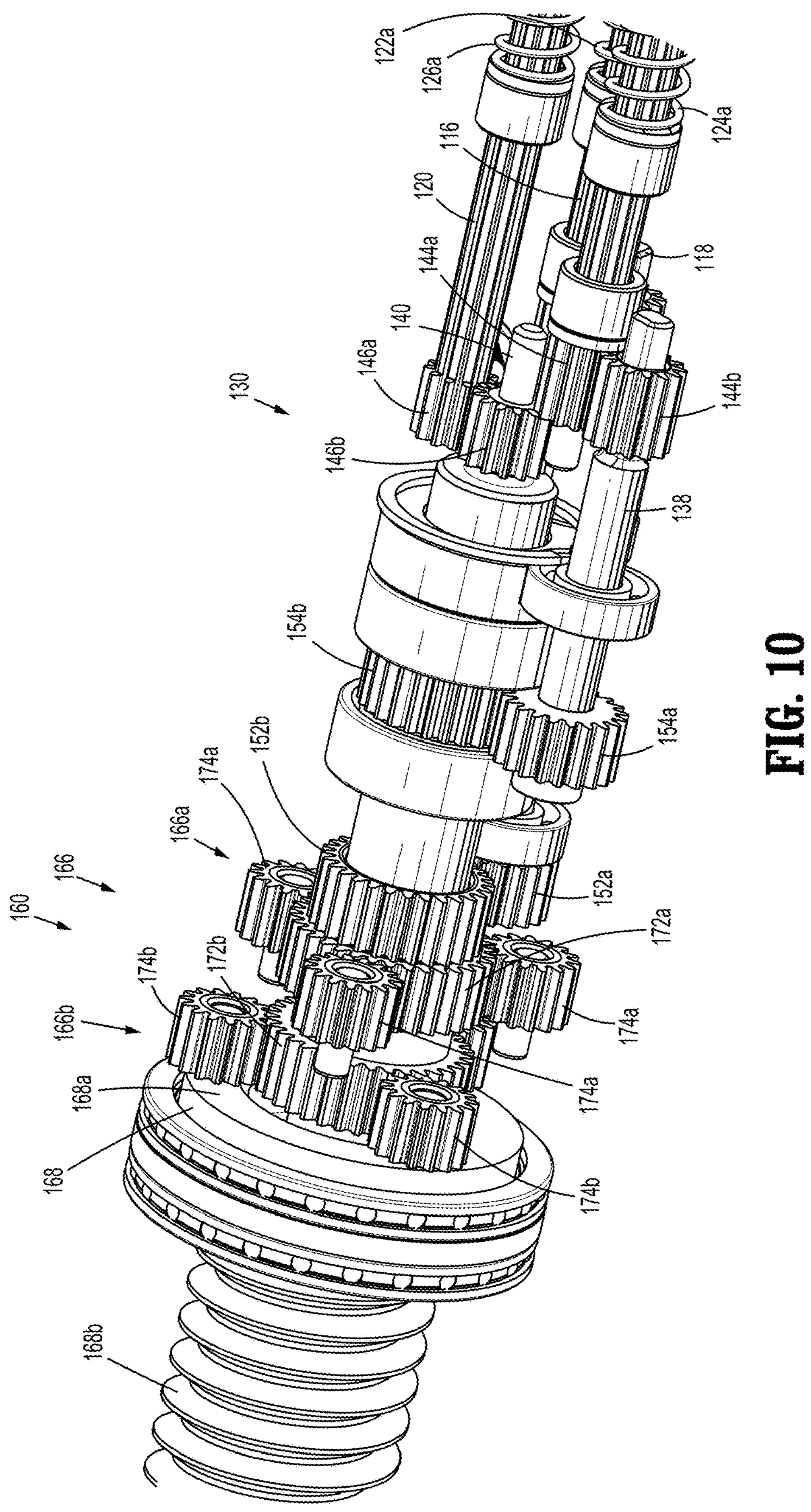
FIG. 10 is an enlarged view of the indicated area of detail of FIG. 9.

With particular reference to FIGS. 9-13, first pusher assembly 160 includes proximal and distal housing sections 162, 164 (FIG. 11), a planetary gear assembly 166 operably mounted within proximal housing section 162, a screw member 168 (FIG. 11) operably connected to planetary gear assembly 166 and rotatably supported within distal housing section 164, and a pusher member 170 (FIG. 11) operably connected screw member 168 and slidably disposed within distal housing section 164. Proximal housing section 162 includes a pair of longitudinal flanges **162*a* (FIG. 4; only one shown) and distal housing section 164 includes a pair of longitudinally flattened portions 164*a*. Each of the flanges 162*a* and the flattened portions 164*a* of respective proximal and distal housing sections 162, 164 engage an inner surface of sleeve 106 to prevent rotation of respective proximal housing section 162 and distal housing section 164 relative to sleeve 106 during operation of surgical device 10. Planetary gear assembly 166 includes first and second planetary gear systems 166*a*, 166*b* (FIG. 10). First planetary gear system 166*a* includes a central drive gear 172*a* mounted on a distal end of drive connector 148 of drive transfer assembly 130 and a plurality of planetary gears 174*a* rotatably mounted to a rotatable support ring 176**.

Each planetary gear **174*a* engages central drive gear 172*a* and a toothed inner surface 165 of proximal housing section 162. As central drive gear 172*a* rotates in a first direction, i.e., clockwise, each planetary gear 174*a* rotates in a second direction, i.e., counter-clockwise. As each planetary gear 174*a* rotates in the second direction, engagement of planetary gears 174*a* with toothed inner surface 165 of distal housing section 162 causes rotatable support ring 176 to rotate in the first direction. Conversely, rotation of central drive gear 172*a* in the second direction causes rotation of each planetary gear 174*a* in the first direction thereby causing rotation of rotatable support ring 176 in the second direction. The configuration of first planetary gear system 166*a* provides a reduction in the gear ratio. In this manner, the speed of rotation of rotatable support ring 174 is less than the speed of rotation of central drive gear 172*a***.

Second planetary gear system **166*b* includes a central drive gear 172*b* securely affixed to rotatable support ring 176 and a plurality of planetary gears 174*b* rotatably mounted to a proximal end surface 168*a* of screw member 168. Each planetary gear 174*b* engages central drive gear 172*b* and toothed inner surface 165 of proximal housing section 162. As rotatable support ring 176 of first planetary gear system 166*a* rotates in the first direction thereby causing central drive gear 172*b* to also rotate in the first direction, each planetary gear 174*b* rotates in the second direction. As each planetary gear 174*b* rotates in the second direction, engagement of planetary gears 174*b* with toothed inner surface 165 of proximal housing section 162 causes screw member 168 to rotate in the first direction. Conversely, rotation of central drive gear 172*b* in the second direction causes rotation of each planetary gear 174*b* in the first direction, thereby causing screw member 168 to rotate in the second direction. The configuration of second planetary gear system 166*b* provides a reduction in the gear ratio. In this manner, the speed of rotation of screw member 168 is less than the speed of rotation of central drive gear 172*b*. First and second planetary gear systems 166*a*, 166*b* operate in unison to provide a reduction in the gear ratio between first rotatable proximal drive shaft 116 and screw member 168. In this manner, the reduction in the speed of rotation of screw member 168 relative to drive connector 148 is a product of the reduction provided by the first and second planetary gear systems 166*a*, 166*b***.

Screw member 168 is rotatably supported within proximal housing portion 162 and includes a threaded distal end **168*b* that operably engages a threaded inner surface 170*a* of pusher member 170. As screw member 168 is rotated in the first direction, engagement of threaded distal end 168*b* of screw member 168 with threaded inner surface 170*a* of pusher member 170 causes longitudinal advancement of pusher member 170, as indicated by arrows "A" in FIG. 12. Conversely, rotation of screw member 168 in the second direction causes retraction of pusher member 170**.

Pusher member 170 includes a pair of tabs 178 formed on a distal end thereof for engaging connector extensions 240, 242 (FIG. 19) of outer flexible band assembly 230 (FIG. 19) of extension assembly 200 (FIG. 17). Although shown as tabs 178, it is envisioned that pusher member 170 may include any structure suitable for selectively engaging connector extensions 240, 242 of outer flexible band 230 of extension assembly 200.

Figures 14, 15:
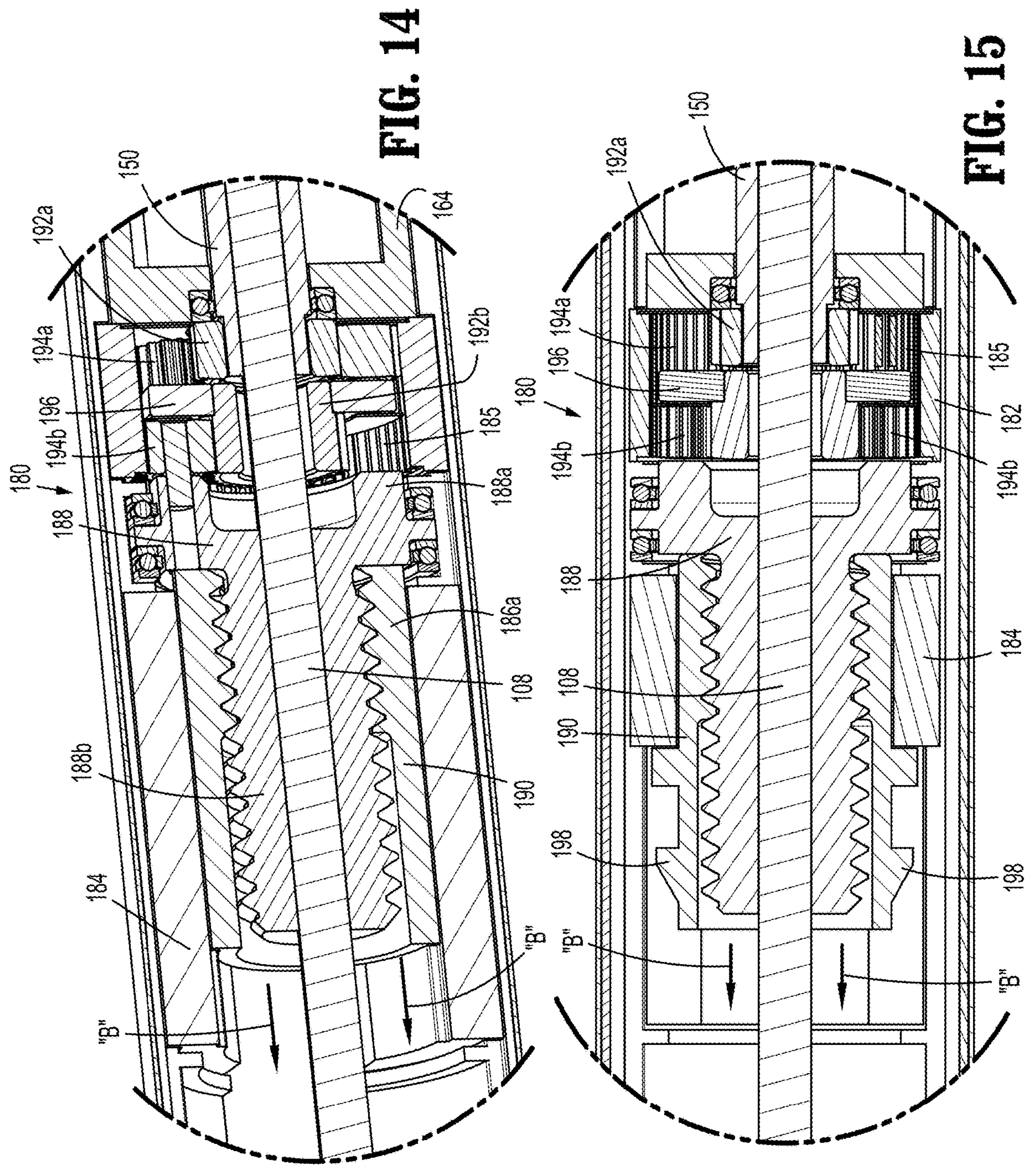
FIG. 14 is an enlarged view of the indicated area of detail of FIG. 6.
FIG. 15 is an enlarged view of the indicated area of detail of FIG. 7.

With particular reference now to FIGS. 14-16, second pusher assembly 180 is substantially similar to first pusher assembly 160, and includes proximal and distal housing sections 182, 184, a planetary gear assembly 186 operably mounted within proximal housing section 182, a screw member 188 operably connected to planetary gear assembly 186 and rotatably supported within distal housing section 184, and a pusher member 190 operably connected to screw member 188 and slidably disposed within distal housing section 184. Each of proximal housing section 182 and distal housing section 184 includes a pair of longitudinal flanges 182*a*, 184*a* (FIG. 4; only one shown), respectively, engage an inner surface of sleeve 106 of adapter assembly 100 to prevent rotation of respective proximal housing section 182 and distal housing section 184 relative to sleeve 106 during operation of surgical device 10. Planetary gear assembly 186 includes first and second planetary gear systems 186*a*, 186*b* (FIG. 16). First planetary gear system 186*a* includes a central drive gear 192*a* mounted on a distal end of tubular connector 150 of drive transfer assembly 130 and a plurality of planetary gears 194*a* rotatably mounted to a rotatable support ring 196.

Each planetary gear 194*a* engages central drive gear 192*a* and a toothed inner surface 185 of proximal housing section 182. As central drive gear 192*a* rotates in a first direction, i.e., clockwise, each planetary gear 194*a* rotates in a second direction, i.e., counter-clockwise. As each planetary gear 194*a* rotates in the second direction, engagement of planetary gears 194*a* with toothed inner surface 185 of distal housing section 182 causes rotatable support ring 196 to rotate in the first direction. Conversely, rotation of central drive gear 192*a* in the second direction causes rotation of each planetary gear 194*a* in the first direction thereby causing rotation of rotatable support ring 196 in the second direction. The configuration of first planetary gear system 186*a* provides a reduction in the gear ratio. In this manner, the speed of rotation of rotatable support ring 194 is less than the speed of rotation of central drive gear 190*a*.

Second planetary gear system 186*b* includes a central drive gear 192*b* securely affixed to rotatable support ring 196 and a plurality of planetary gears 194*b* rotatably mounted to a proximal end surface 188*a* of screw member 188. Each planetary gear 194*b* engages central drive gear 192*b* and toothed inner surface 185 of proximal housing section 182. As rotatable support ring 196 of first planetary gear system 186*a* rotates in the first direction thereby causing central drive gear 192*b* to also rotate in the first direction, each planetary gear 174*b* rotates in the second direction. As each planetary gear 194*b* rotates in the second direction, engagement of planetary gears 194*b* with toothed inner surface 185 of proximal housing section 182 causes screw member 188 to rotate in the first direction. Conversely, rotation of central drive gear 192*b* in the second direction causes rotation of each planetary gear 194*b* in the first direction, thereby causing screw member 198 to rotate in the second direction. The configuration of second planetary gear system 186*b* provides a reduction in the gear ratio. In this manner, the speed of rotation of screw member 188 is less than the speed of rotation of central drive gear 182*b*. First and second planetary gear systems 186*a*, 186*b* operate in unison to provide a reduction in the gear ratio between second rotatable proximal drive shaft 118 and screw member 188. In this manner, the reduction in the speed of rotation of screw member 188 relative to tubular connector 150 is a product of the reduction provided by the first and second planetary gear systems 186*a*, 186*b*.

Screw member 188 is rotatably supported within proximal housing portion 182 and includes a threaded distal end 188*b* that operably engages a threaded inner surface 190*a* of pusher member 190. As screw member 188 is rotated in the first direction, engagement of threaded distal end 188*b* of screw member 188 with threaded inner surface 190*a* of pusher member 190 causes longitudinal advancement of pusher member 190. Conversely, rotation of screw member 188 in the second direction causes retraction of pusher member 190. Pusher member 190 includes a pair of longitudinal flanges 191 (FIG. 5; only one shown) that engage distal housing section 184 of second pusher assembly 180 for preventing rotation of pusher member 190 relative distal housing section 184.

Pusher member 190 includes a pair of tabs 198 formed on a distal end thereof for engaging connector extensions 220, 224 (FIG. 18) of inner flexible band assembly 210 (FIG. 18) of extension assembly 200 (FIG. 17). Although shown as tabs 198, it is envisioned that pusher member 190 may include any structure suitable for selectively engaging connector extensions 240, 242 of outer flexible band 230 of extension assembly 200.

Extension assembly 200 for operably connecting adapter assembly 100 (FIG. 3) with a circular loading unit, e.g. loading unit 40 (FIG. 34) and an anvil assembly, e.g., anvil assembly 50 (FIG. 34) will be described with reference now to FIGS. 17-34. In particular, a proximal end 202 of extension assembly 200 operably connects with distal end 104 (FIG. 3) of adapter assembly 100 (FIG. 3) and a distal end 204 of extension assembly 200 operably connects with loading unit 40 and anvil assembly 50. As shown, extension assembly 200 provides a slight curvature between proximal and distal end 202, 204. In alternative embodiment, extension assembly 200 may be straight or may include a greater curvature. Although extension assembly 200 will be shown and described as being used to connect loading unit 40 and anvil assembly 50 to adapter assembly 100 (FIG. 3), it is envisioned that the aspects of the present disclosure may be modified for use with various loading units, anvil assemblies, and adapter assemblies. Exemplary loading units and anvil assemblies are described in commonly owned U.S. Pat. No. 8,590,763and U.S. patents application Ser. Nos. 14/056,301 and 14/149,355, the contents of each being incorporated herein by reference in their entirety.

Extension assembly 200 includes an inner flexible band assembly 210 (FIG. 18), about an outer flexible band assembly 230 (FIG. 19) slidably disposed about inner flexible band assembly 210, a frame assembly 250 (FIG. 20) for supporting inner and outer flexible band assemblies 210, 230, a trocar assembly 270 (FIG. 29) operably received through inner and outer flexible band assemblies 210, 230, and a connector assembly 290 for securing loading unit 40 (FIG. 34) to extension assembly 200. An outer sleeve 206 (FIG. 17) is received about frame assembly 250 and trocar assembly 270 and inner and outer flexible band assemblies 210, 230 are slidably received through outer sleeve 206. As will be described in further detail below, extension assembly 200 may include a drive shaft 208 operably connected to trocar assembly 270 and extending through proximal end 202 of extension assembly 200.

Figures 18, 19:
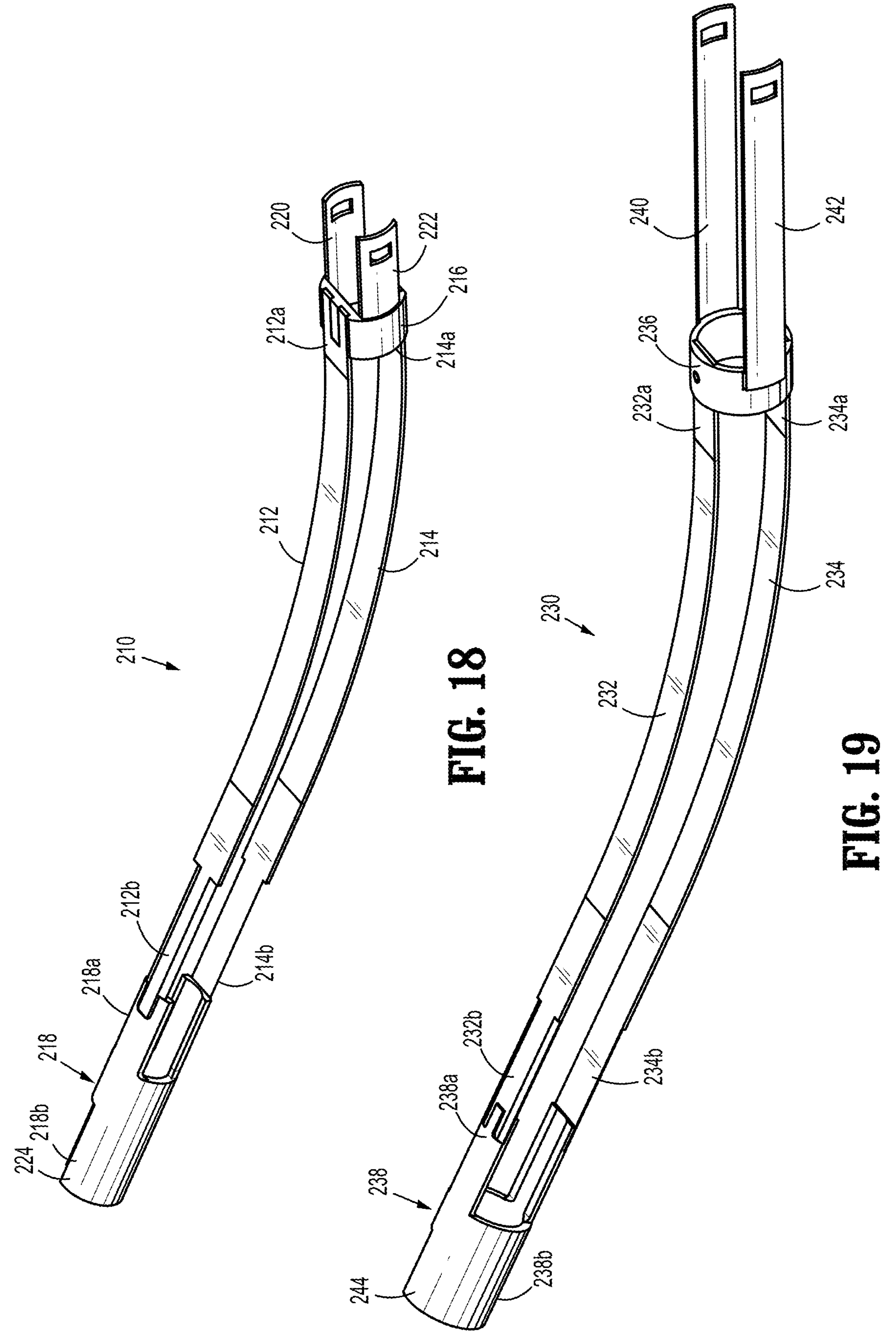
FIG. 18 is a perspective side view of an inner flexible band assembly of the extension assembly of FIG. 17.
FIG. 19 is a perspective side view of an outer flexible band assembly of the extension assembly of FIG. 17.
Figure 20:
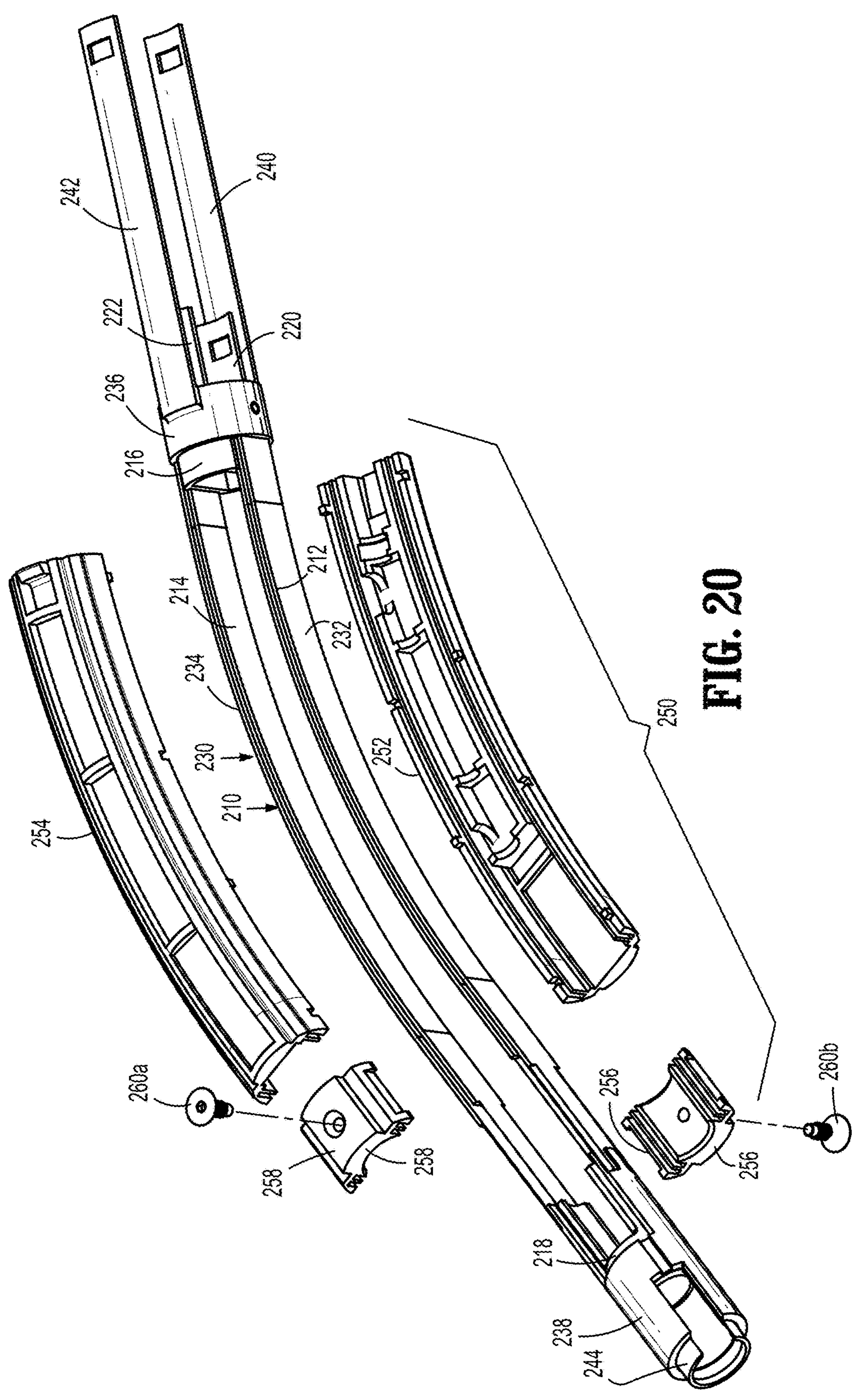
FIG. 20 is a perspective side view of the inner and outer flexible band assemblies of FIGS. 18 and 19 and an exploded view of a frame assembly of the extension assembly of FIG. 17.
Figures 21, 22:
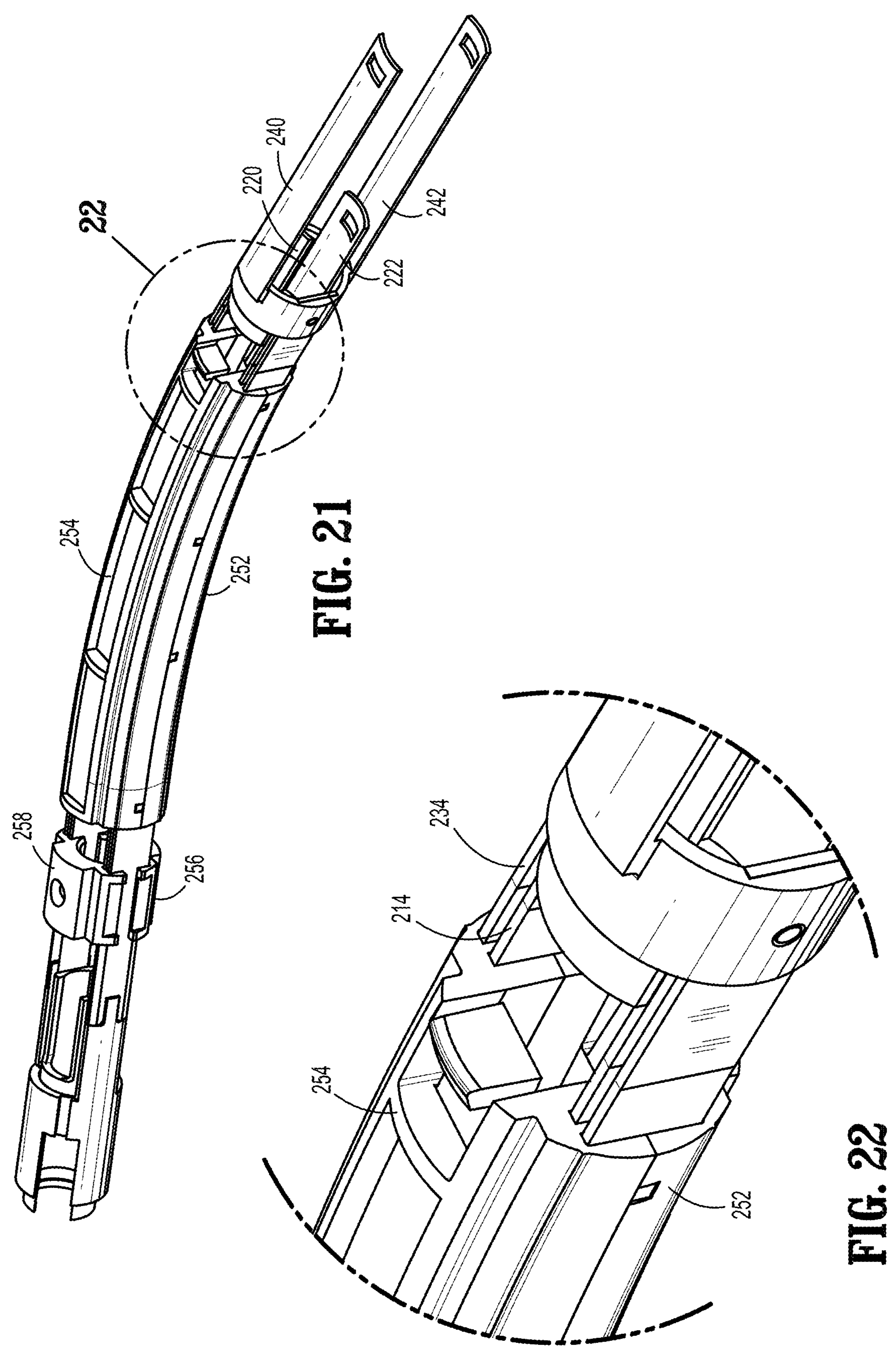
FIG. 21 is a perspective side view of the inner and outer flexible band assemblies and frame assembly of FIG. 20.
FIG. 22 is an enlarged view of the indicated area of detail of FIG. 21.
Figures 23, 24:
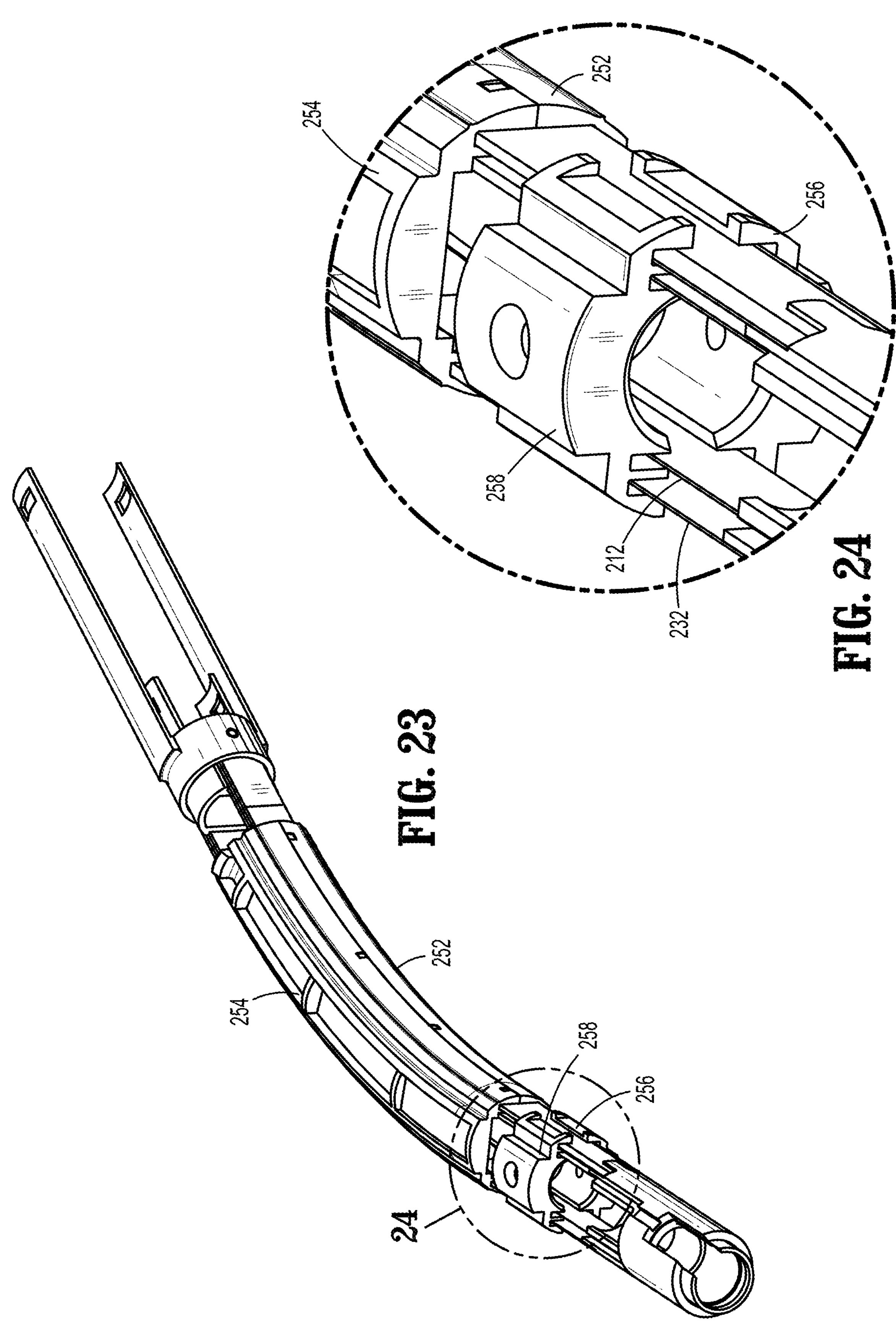
FIG. 23 is a front, perspective view of the inner and outer flexible band assemblies and frame assembly of FIG. 20.
FIG. 24 is an enlarged view of the indicated area of detail of FIG. 23.
Figure 25:
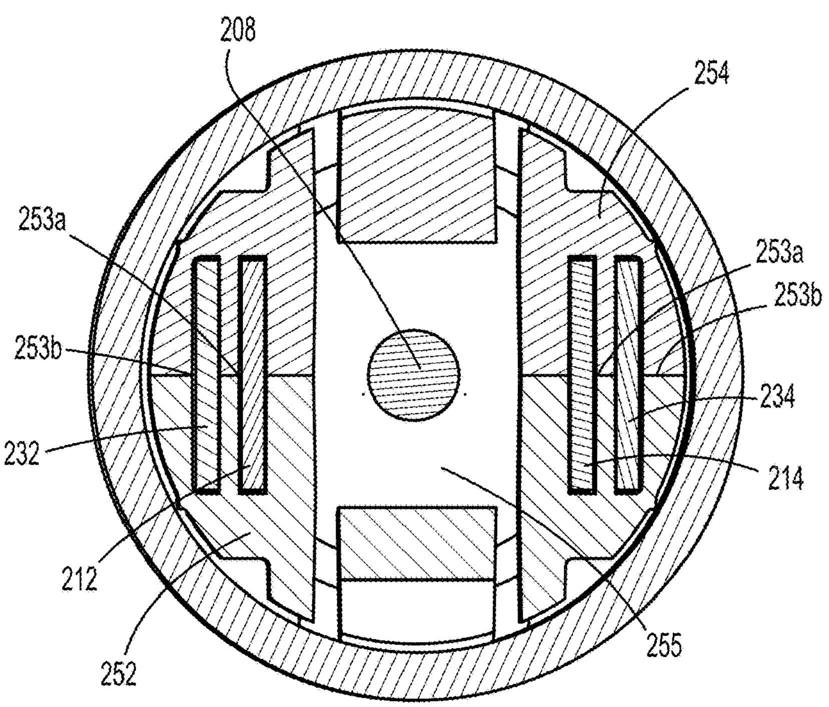
FIG. 25 is a cross-sectional end view taken along line 25-25 of FIG. 17.

With reference to FIG. 18, inner flexible band assembly 210 includes first and second inner flexible bands 212, 214, a support ring 216, a support base 218, and first and second connection extensions 220, 222. Proximal ends 212*a*, 214*a* of respective first and second inner flexible bands 212, 214 are laterally spaced apart and securely attached to support ring 216. Distal ends 212*b*, 214*b* of first and second inner flexible bands 212, 214 are laterally spaced apart and securely attached to a proximal end 218*a* of support base 218. Each of first and second inner flexible bands 212, 214 may be attached to support ring 216 and/or support base 218 in any suitable manner, including, for example, by press-fitting, welding, adhesives, and/or with mechanical fasteners. As will be described in further detail below, inner flexible band assembly 210 is configured to be slidably received about trocar assembly 270 (FIG. 28) and within outer flexible band assembly 230 (FIG. 19) and outer sleeve 206 (FIG. 17).

First and second connection extensions 220, 222 of inner flexible band assembly 210 extend proximally from support ring 216 and operably connect inner flexible band assembly 210 with pusher member 190 (FIG. 15) of second pusher assembly 180 (FIG. 15) of adapter assembly 100 (FIG. 3). In particular, each of first and second connection extensions 220, 222 define openings 221, 223 configured to receive tabs 198 (FIG. 15) of pusher member 190 (FIG. 15) of second pusher assembly 180. Receipt of tabs 198 of pusher member 190 within openings 221, 223 of respective first and second extensions 220, 222 secure inner flexible band assembly 210 of extension assembly 200 with second pusher assembly 180 of adapter assembly 100. First and second connection extensions 220, 222 may be integrally formed with support ring 216, or attached thereto in any suitable manner.

Figure 34:
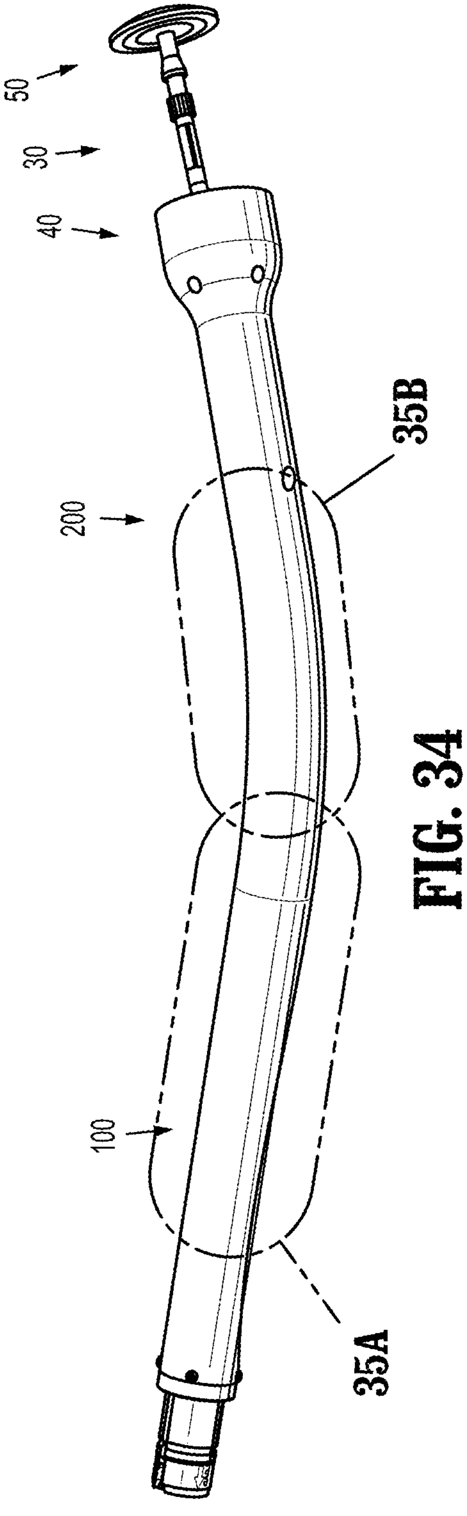
FIG. 34 is a perspective side view of the adapter assembly of FIG. 3 connected to the extension assembly of FIG. 17 and an end effector and an anvil assembly connected to the extension assembly.

Support base 218 extends distally from inner flexible bands 212, 214 and is configured to selectively connect extension assembly 200 with loading unit 40 (FIG. 34). Specifically, a distal end 218*b* 218*a* of support base 218 includes a flange 224 for operable engagement with an axially movable assembly (not shown) of loading unit 40 (FIG. 34). In one embodiment, flange 224 is configured for connection with a knife assembly (not shown) of loading unit 40 (FIG. 34).

With reference now to FIG. 19, outer flexible band assembly 230 is substantially similar to inner flexible band assembly 210 and includes first and second flexible bands 232, 234 laterally spaced and connected on proximal ends 232*a*, 234*a* to a support ring 236 and on distal ends 232*b*, 234*b* to a proximal end 238*a* of a support base 238. Each of first and second outer flexible bands 232, 234 may be attached to support ring 236 and support base 238 in any suitable manner, including, for example, by press-fitting, welding, adhesives, and/or with mechanical fasteners. As will be described in further detail below, outer flexible band assembly 230 is configured to receive trocar assembly 270 (FIG. 28) therethrough.

First and second connection extensions 240, 242 of outer flexible band assembly 230 extend proximally from support ring 236 and operably connect outer flexible band assembly 230 with pusher member 170 (FIG. 12) of first pusher assembly 160 (FIG. 12) of adapter assembly 100 (FIG. 1). In particular, each of first and second connection extensions 240, 242 define openings 241, 243 configured to receive tabs 178 (FIG. 12) of pusher member 170 of first pusher assembly 180. Receipt of tabs 178 of pusher member 170 within openings 241, 243 of respective first and second extensions 240, 242 secures outer flexible band assembly 230 of extension assembly 200 with first pusher assembly 180 of adapter assembly 100. First and second connection extensions 240, 242 may be integrally formed with support ring 236, or attached thereto in any suitable manner.

Support base 238 extends distally from outer flexible bands 232, 234 and is configured to selectively connect extension assembly 200 with loading unit 40 (FIG. 34). Specifically, a distal end 238*b* of support base 238 includes a flange 244 for operable engagement with an axially movable assembly (not shown) of a loading unit (not shown). In one embodiment, flange 244 is configured for connection with a staple pusher assembly (not shown) of loading unit 40 (FIG. 34).

With reference now to FIGS. 20-26, frame assembly 250 includes first and second proximal spacer members 252, 254, and first and second distal spacer members 256, 258. When secured together, first and second proximal spacer members 252, 254 define a pair of inner longitudinal slots 253*a* for slidably receiving first and second flexible bands 212, 214 (FIG. 18) of inner flexible band assembly 210 (FIG. 18) and a pair of outer longitudinal slots 253*b* for slidably receiving first and second flexible bands 232, 234 (FIG. 19) of outer flexible band assembly 230 (FIG. 19). First and second proximal spacer members 252, 254 further define a longitudinal passage 255 for receipt of trocar assembly 270.

In one embodiment, and as shown, first and second proximal spacer members 252, 254 are formed of plastic and are secured together with a snap-fit arrangement. Alternatively, first and second proximal spacer members 252, 254 may be formed of metal or other suitable material and may be secured together in any suitable manner, including by welding, adhesives, and/or using mechanical fasteners.

First and second distal spacer members 256, 258 define a pair of inner slots 257*a* for slidably receiving first and second flexible bands 212, 214 (FIG. 18) of inner flexible band assembly 210 (FIG. 18) and a pair of outer slots 257*b* for slidably receiving first and second flexible bands 232, 234 (FIG. 19) of outer flexible band assembly 230 (FIG. 19). First and second distal spacer members 256, 258 further define a longitudinal passage 259 for receipt of trocar assembly 270.

Figure 26:
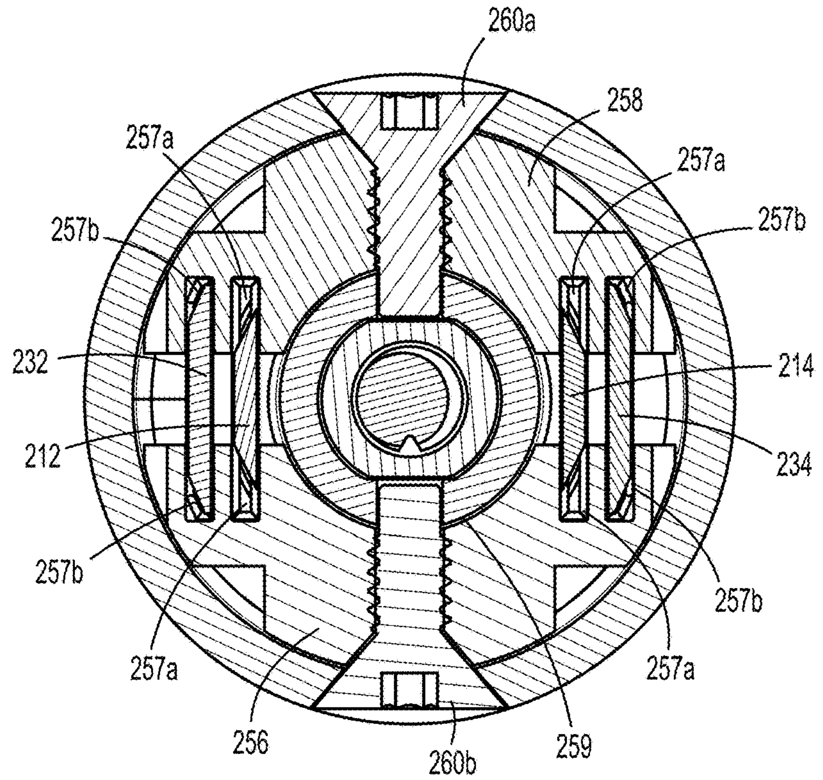
FIG. 26 is a cross-sectional end view taken along line 26-26 of FIG. 17.

In one embodiment, and as shown, each of first and second distal spacer members 256, 258 are secured about inner and outer flexible band assemblies 210, 230 and to outer sleeve 206 (FIG. 17) by a pair of screws 260*a*, 260*b* (FIG. 26). Alternatively, first and second distal spacer members 256, 258 may be secured together in any suitable manner, including by welding, adhesives, and/or using mechanical fasteners. First and second distal spacer members 256, 258 may be formed of metal or any other suitable material.

Figures 27, 28:
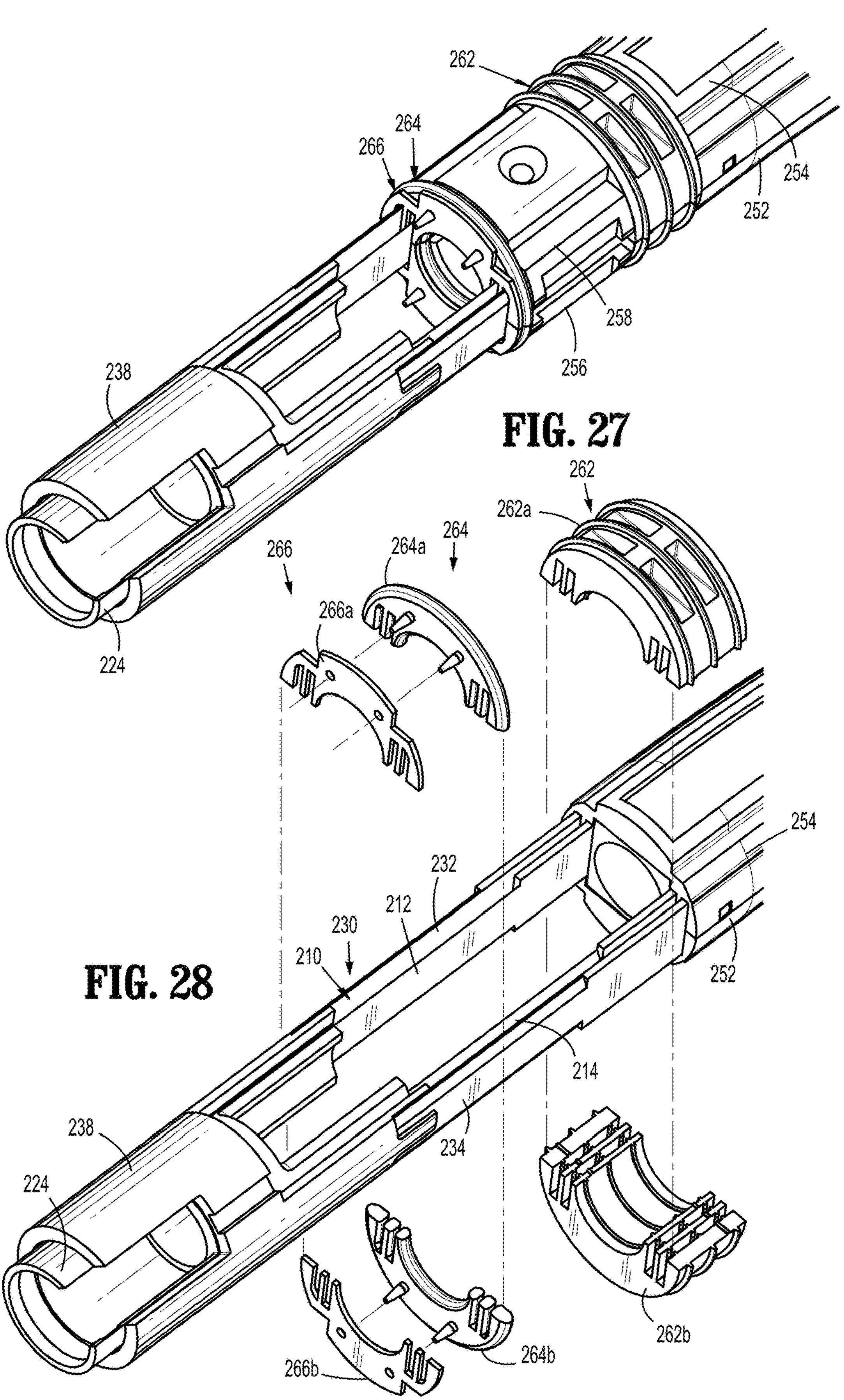
FIG. 27 is an enlarged perspective side view of a distal end of the inner and outer flexible band assemblies and frame assembly of FIG. 20 including a proximal seal member and first and second distal seal members.
FIG. 28 is an exploded perspective view of the proximal seal member and first and second distal seal members of FIG. 27.

With reference now to FIGS. 27 and 28, frame assembly 250 further includes a proximal seal member 252 and first and second distal seal members 264, 266. Each of proximal seal member 252 and first and second distal seal members 264, 266 include seals halves 262*a*, 262*b*, 264*a*, 264*b*, 266*a*, 266*b*, respectively. Proximal seal member 262 is received between first and second proximal spacer members 252, 254 and first and second distal spacer members 256, 258. First half 264*a* of first distal seal member 264 is secured to first half 266*a* of second distal seal member 266 and second half 264*b* of first distal seal member 264 is secured to second half of second distal seal member 266. Proximal seal member 262 and first and second distal seal members 264, 266 engage outer sleeve 206 (FIG. 17), inner and outer flexible bands 212, 214 and 232, 234 of respective inner and outer flexible band assemblies 210, 230 and trocar assembly 270 (FIG. 28) in a sealing manner. In this manner, proximal seal member 262 and first and second distal seal members 264, 266 operate to provide a fluid tight seal between distal end 204 and proximal end 202 of extension assembly 200.

With reference to FIGS. 29-32, trocar assembly 270 of extension assembly 200 includes an outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274*a* having an inner threaded portion 273 which engages a threaded distal portion 276*b* of drive screw 276. As drive screw 276 is rotated within trocar member 274, engagement of inner threaded portion 273 of trocar member 274 with threaded distal portion 276*b* of drive screw 276 causes longitudinal movement of trocar member 274 within outer housing 272 of trocar assembly 270. Rotation of drive screw 276 in a first direction causes longitudinal advancement of trocar member 274 and rotation of drive screw 276 in a second direction causes longitudinal retraction of trocar member 274. A distal end 274*b* of trocar member 274 is configured to selectively engage anvil assembly 50 (FIG. 34).

A bearing assembly 278 is mounted to a proximal end 272*a* of outer housing 272 of trocar assembly 270 for rotatably supporting a proximal end 276*a* of drive screw 276 relative to outer housing 272 and trocar member 274. Bearing assembly 278 includes a housing 278*a*, proximal and distal spacers 278*b*, proximal and distal retention clips 278*c*, proximal and distal bearings 278*d*, and a washer 278*e*. As shown, proximal end 276*a* of drive screw 276 includes a flange 276*c* for connection with a link assembly 280.

Figures 11, 12:
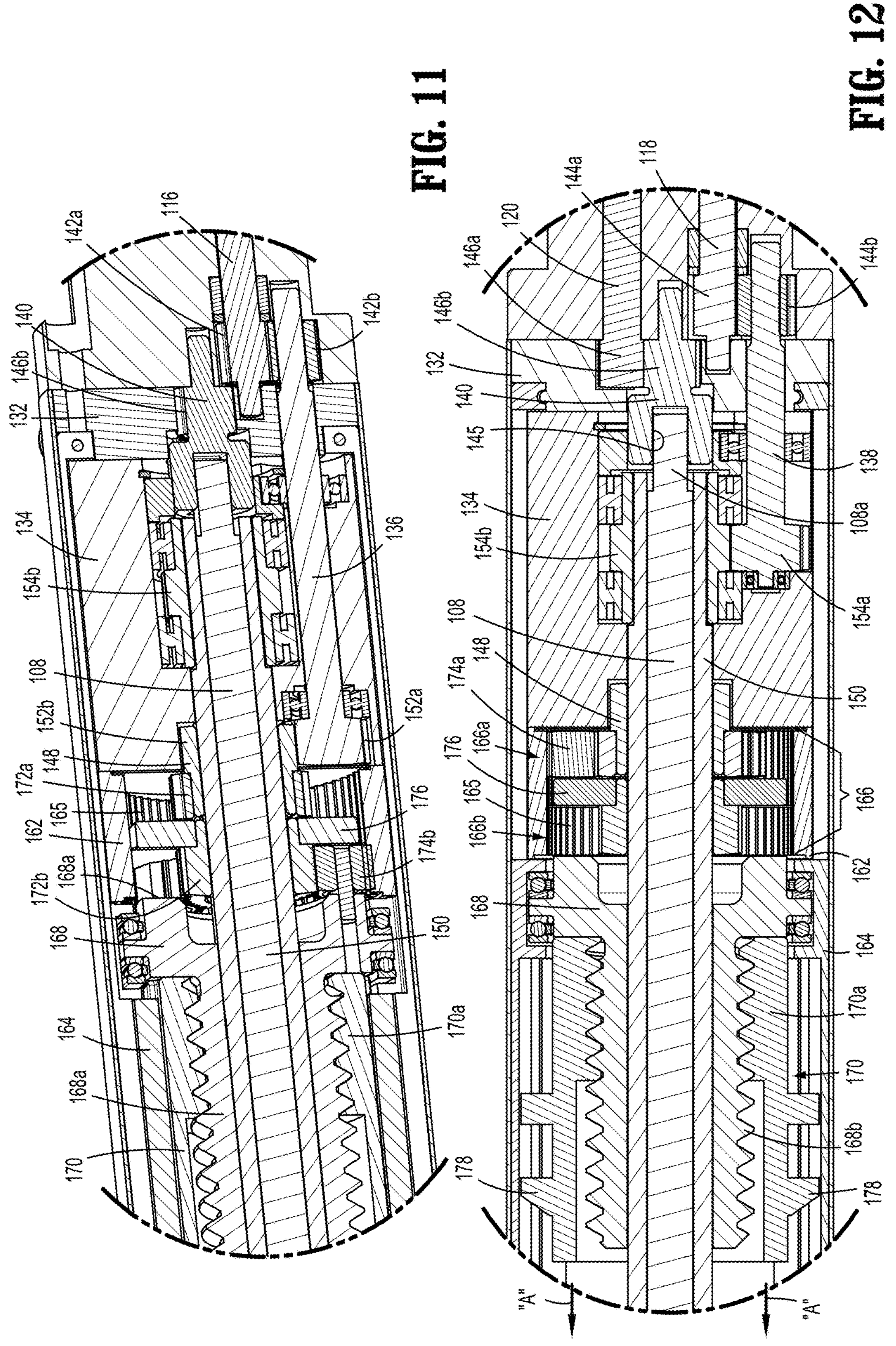
FIG. 11 is an enlarged view of the indicated area of detail of FIG. 6.
FIG. 12 is an enlarged view of the indicated area of detail of FIG. 7.
Figure 13:
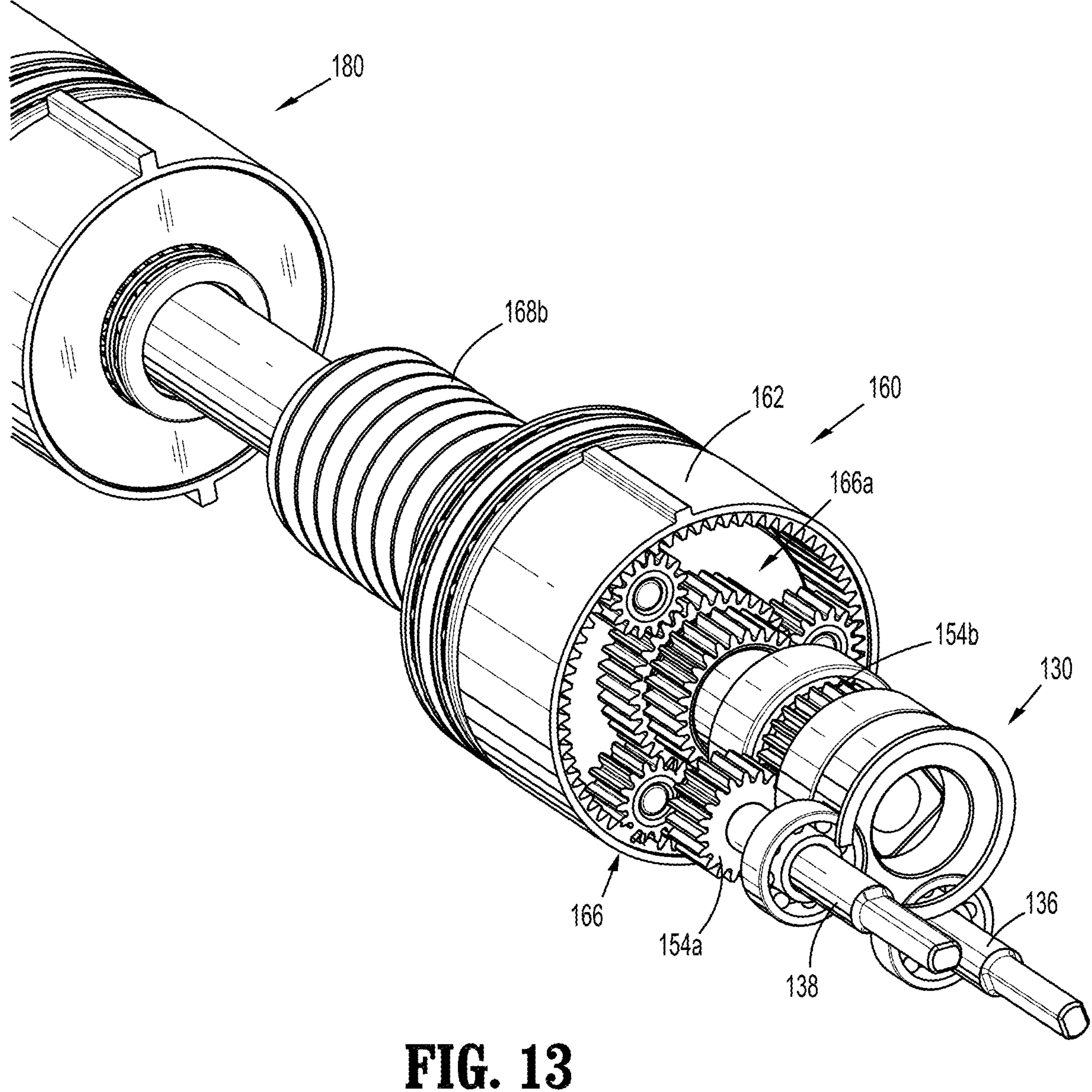
FIG. 13 is a perspective end view of the transfer assembly of FIG. 8.
Figures 32, 33:
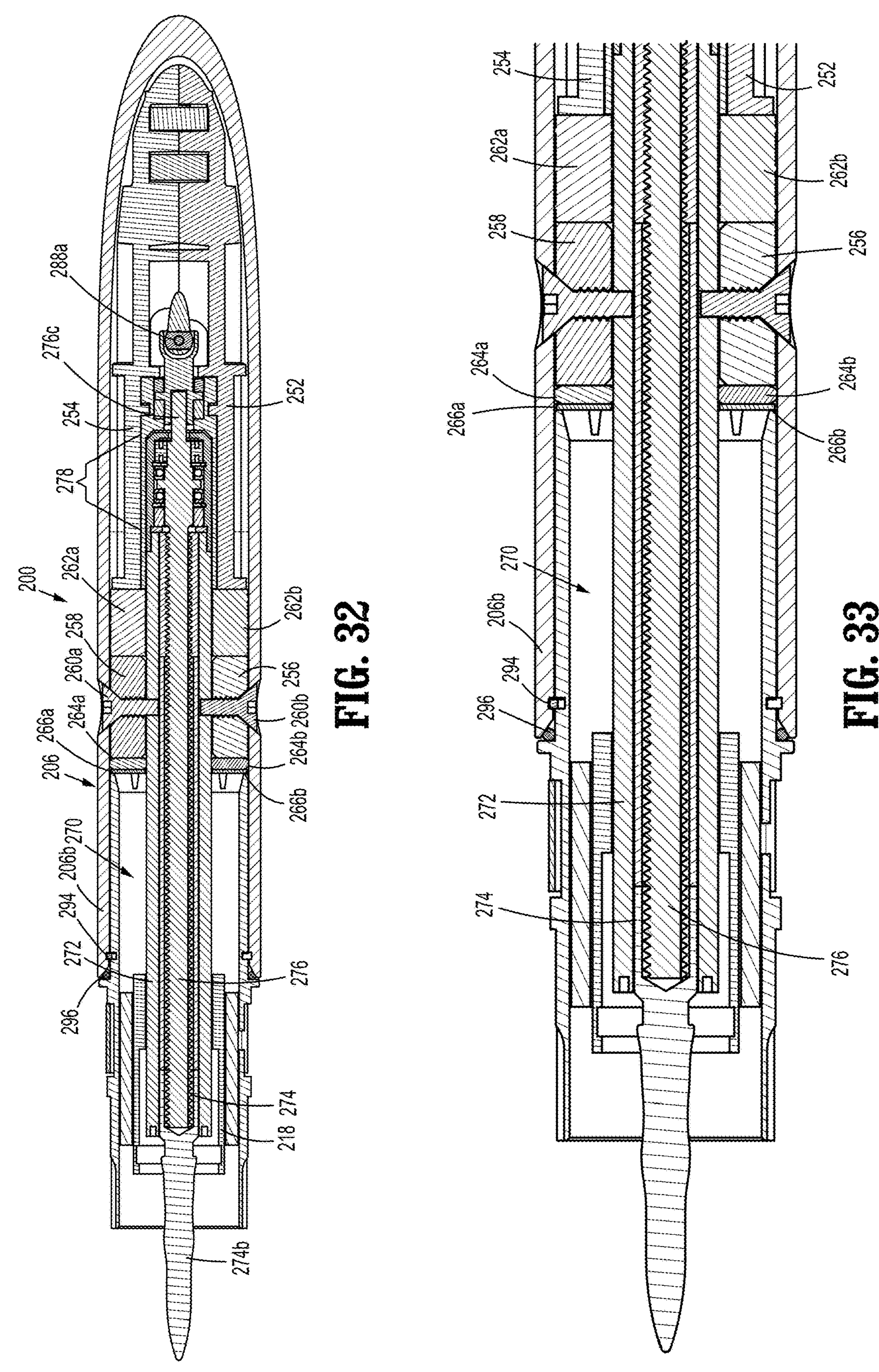
FIG. 32 is a cross-sectional top view taken along line 32-32 of FIG. 17.
FIG. 33 is an enlarged cross-sectional view of the distal end of the extension assembly of FIG. 17.

Link assembly 280 operably connects transfer assembly 130 (FIG. 6) of adapter assembly 100 with trocar assembly 270 (FIG. 30) of extension assembly 200. More particularly, link assembly 280 transfers rotational energy from drive member 140 (FIG. 6) of transfer assembly 130 of adapter assembly 100 through the curved outer tube 206 (FIG. 17) of extension assembly 200 to flange 276*c* (FIG. 29) on proximal end 276*a* of drive screw 276 of trocar assembly 270 of extension assembly 200, with reference to FIGS. 29A and 29B, link assembly 280 includes a coupling member 282, a first drive shaft 284, and a second drive shaft 286. A proximal end 282*a* of coupling member 282 defines a recess 283*a* for receiving a distal end 284*b* of first drive shaft 284. A distal end 282*b* of coupling member 282 defines a recess 283*a* for operably receiving flange 276*c* on proximal end 276*a* of drive screw 276. Coupling member 282 includes an annular flange 282*c* for rotatably receiving coupling member 282 between first and second proximal spacer members 252, 254 (FIG. 32). Proximal and distal ends 284*a*, 284 of first drive shaft 284 define oversized openings 285*a*, 285*b*, respectively, for receiving pins 288*a*, 288*b*, respectively. A distal end 286*b* of second drive shaft 286 defines a recess 287 for operably receiving proximal end 284*a* of drive shaft 284. A proximal end 286*a* of drive shaft 286 includes a flange 286*c* for operable receipt within socket 145 of drive member 140 of drive transfer assembly 130 of adapter assembly 100 (FIG. 12).

Figure 29:
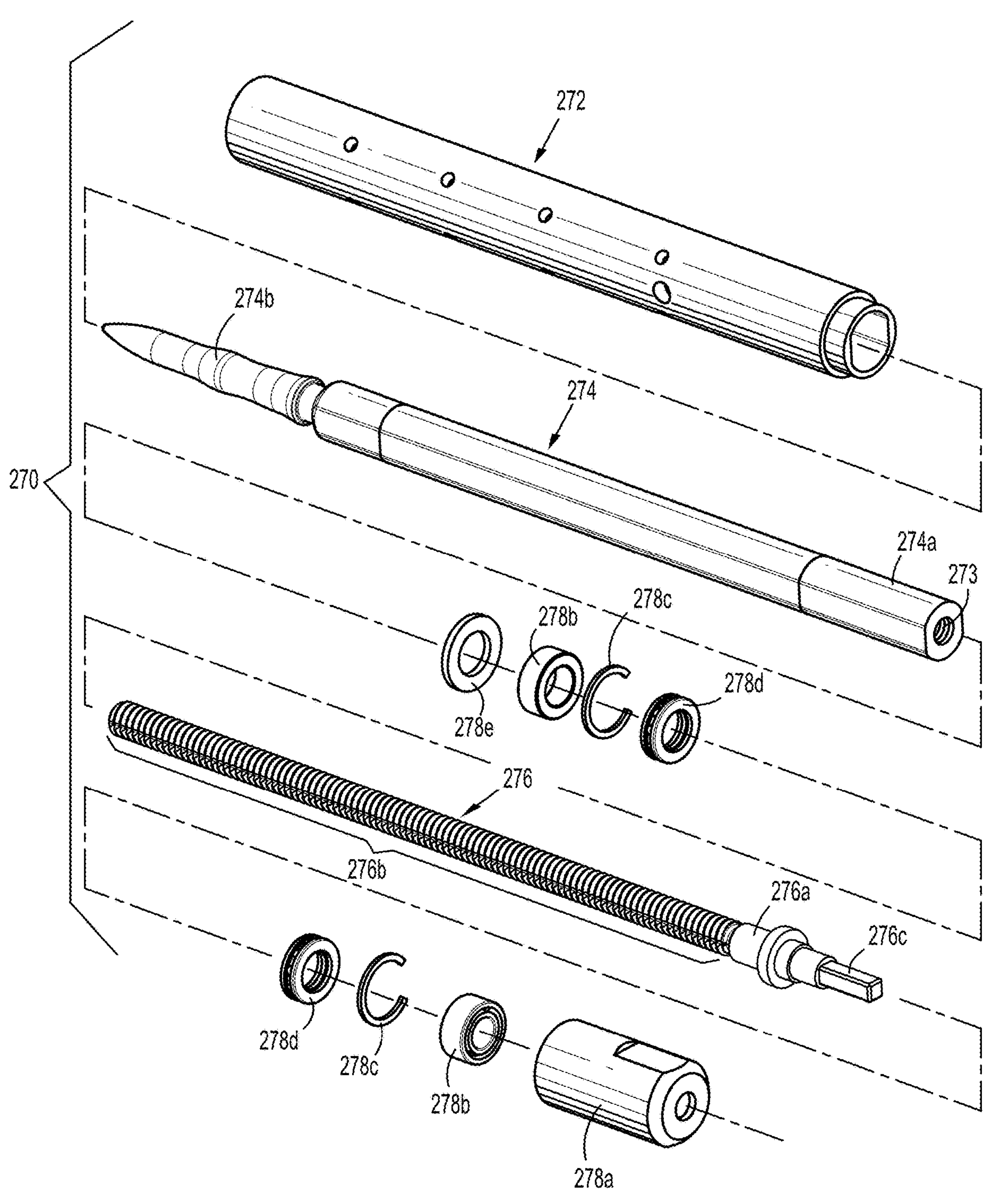
FIG. 29 is an exploded view of a trocar assembly of the extension assembly of FIG. 17.
Figures 29A, 29B:
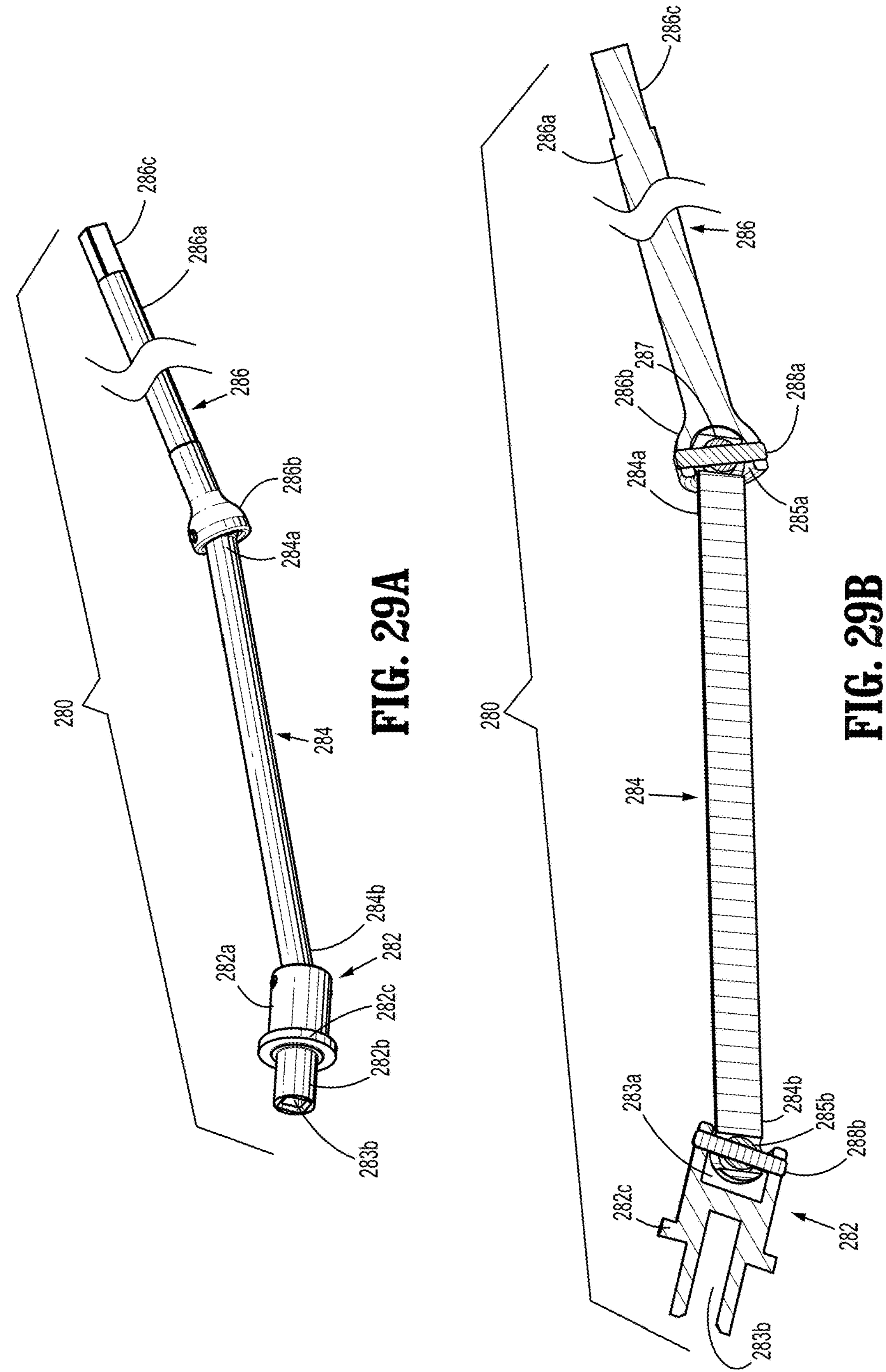
FIG. 29A is a perspective side view of a link assembly of the extension assembly of FIG. 17.
FIG. 29B is a cross-sectional side view of the link assembly of FIG. 29A.
Figures 30, 31:
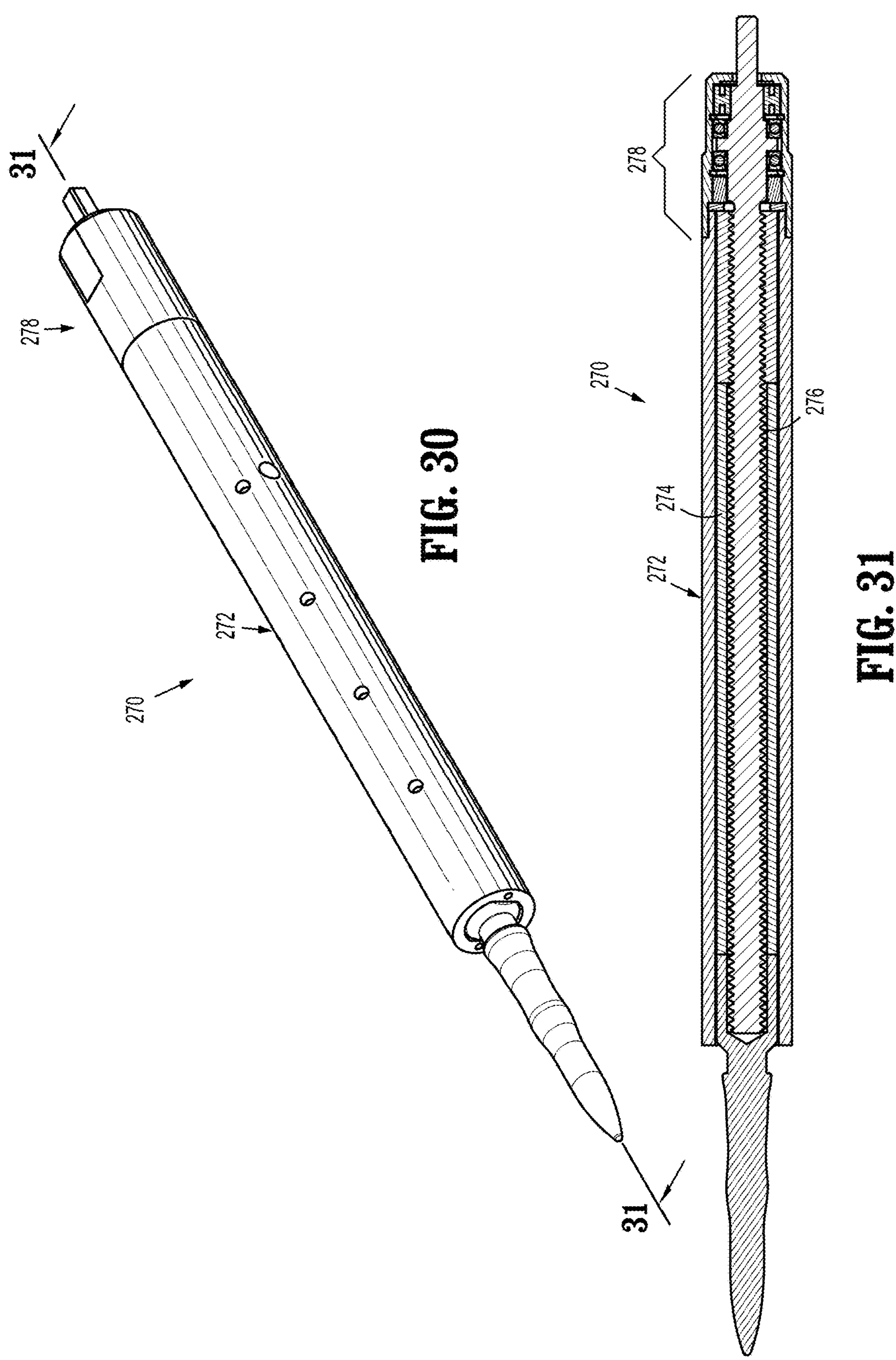
FIG. 30 is a perspective side view of the trocar assembly of FIG. 29.
FIG. 31 is a cross-sectional side view taken along line 31-31 of FIG. 30.

With particular reference to FIG. 29B, proximal end 284*a* of first drive shaft 284 is operably received within recess 287 in distal end 286*b* of second drive shaft 286. Distal end 284*b* of first drive shaft 284 is pivotally secured within recess 283*a* of coupling member 282 by pin 288*a* received through oversized opening 285*b* in distal end 284*b* of first drive shaft 284. Proximal end 284*a* of first drive shaft 284 is pivotally secured within recess 287 in distal end 286*b* of second drive shaft 286 by pin 288*b* received through oversized opening 285*a* in proximal end 284*a* of first drive shaft 284. Recesses 283*a* and 287 of coupling member 282 and second drive shaft 286, respectively, and oversized openings 285*a*, 285*b* of first drive shaft 284 are configured to permit pivoting of second drive shaft 286 relative to first drive shaft 284 and pivoting of first drive shaft 284 relative to coupling member 282 as each of first and second drive shaft 284, 286, and coupling member 282 are rotated about their respective longitudinal axes to transfer rotational force from transfer assembly 130 (FIG. 6) of adapter assembly 100 to trocar assembly 270 (FIG. 30) of extension assembly 200.

With reference now to FIGS. 32 and 33, connector assembly 290 of extension assembly 200 includes a tubular connector 292 attached to a distal end 206*b* of outer sleeve 206 and about distal ends of inner and outer flexible assemblies 210, 230 (FIG. 26) and trocar assembly 270. In particular, a proximal end 292*a* of tubular connector 292 is received within and securely attached to distal end 206*b* of outer sleeve 206 by a retaining clip 294. An O-ring 296 forms a fluid tight seal between tubular connector 292 of connector assembly 290 and outer sleeve 206. A distal end 292*b* of tubular connector 292 is configured to selectively engage a proximal end of loading unit 40 (FIG. 34). Distal end 292*b* of tubular connector 292 engages the circular loading unit with a snap-fit arrangement, bayonet coupling, or in another suitable manner.

Figures 35A, 35B:
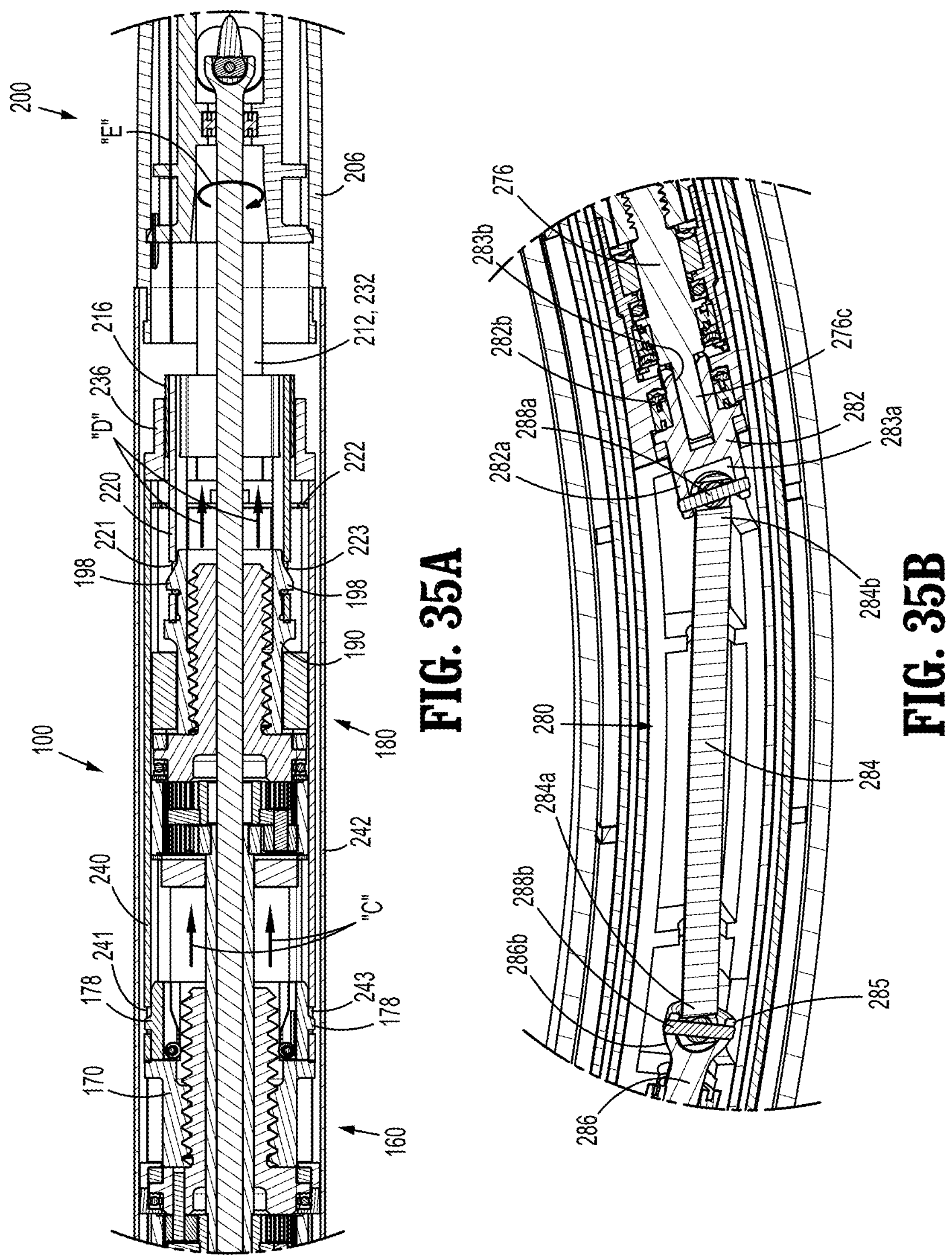
FIG. 35A is an enlarged cross-sectional top view of the indicated area of detail of FIG. 34.
FIG. 35B is an enlarged cross-sectional side view of the indicated area of detail in FIG. 34.
Figure 36:
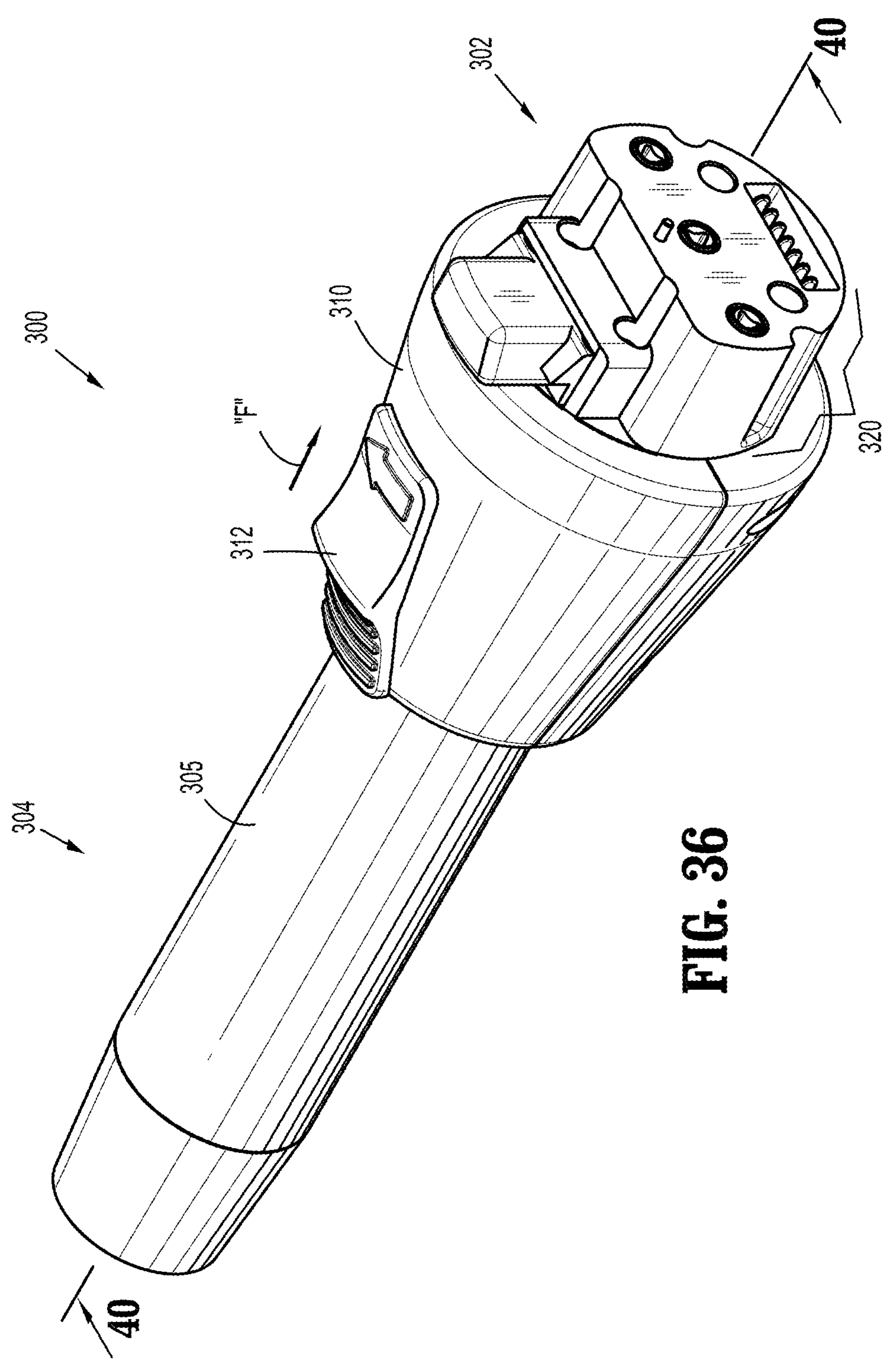
FIG. 36 is a rear, perspective view of an adapter assembly according to another embodiment of the present disclosure.
Figure 37:
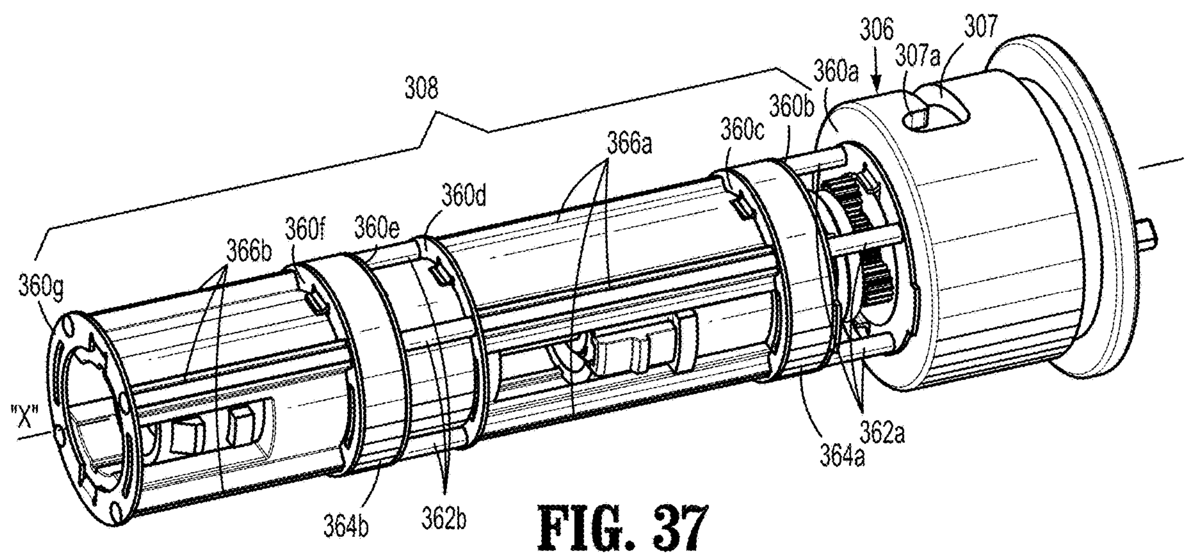
FIG. 37 is a perspective side view of the adapter assembly of FIG. 36 with an outer sleeve and a handle member removed.
Figure 38:
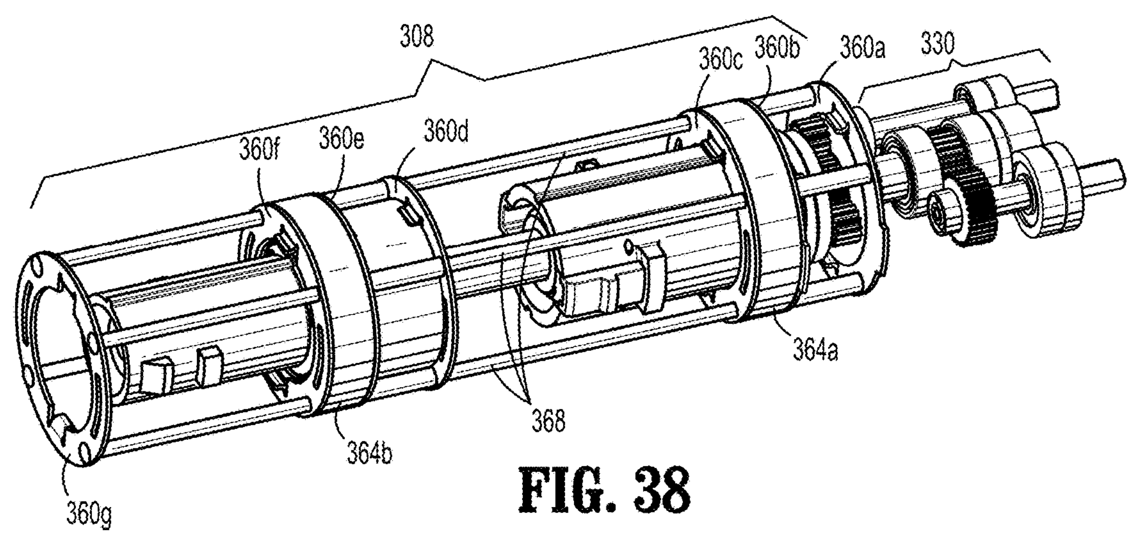
FIG. 38 is a perspective side view of adapter assembly of FIG. 37 with a base and housing members removed.
Figure 39:
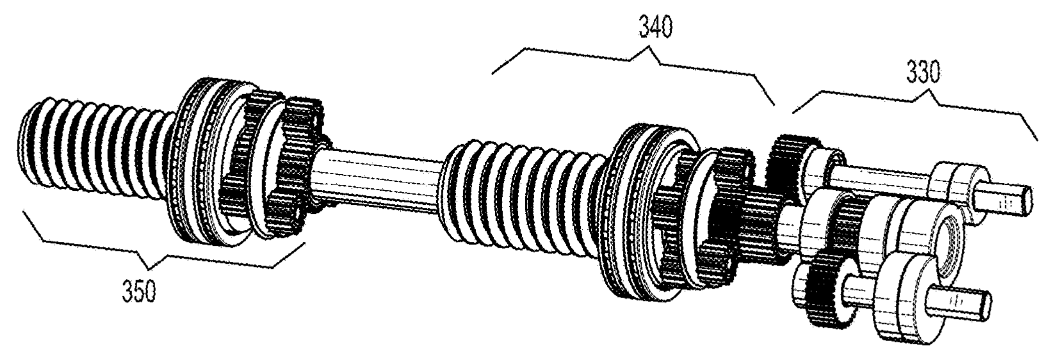
FIG. 39 is a perspective side view of the adapter assembly of FIG. 38 with a support structure removed.
Figures 40, 41:
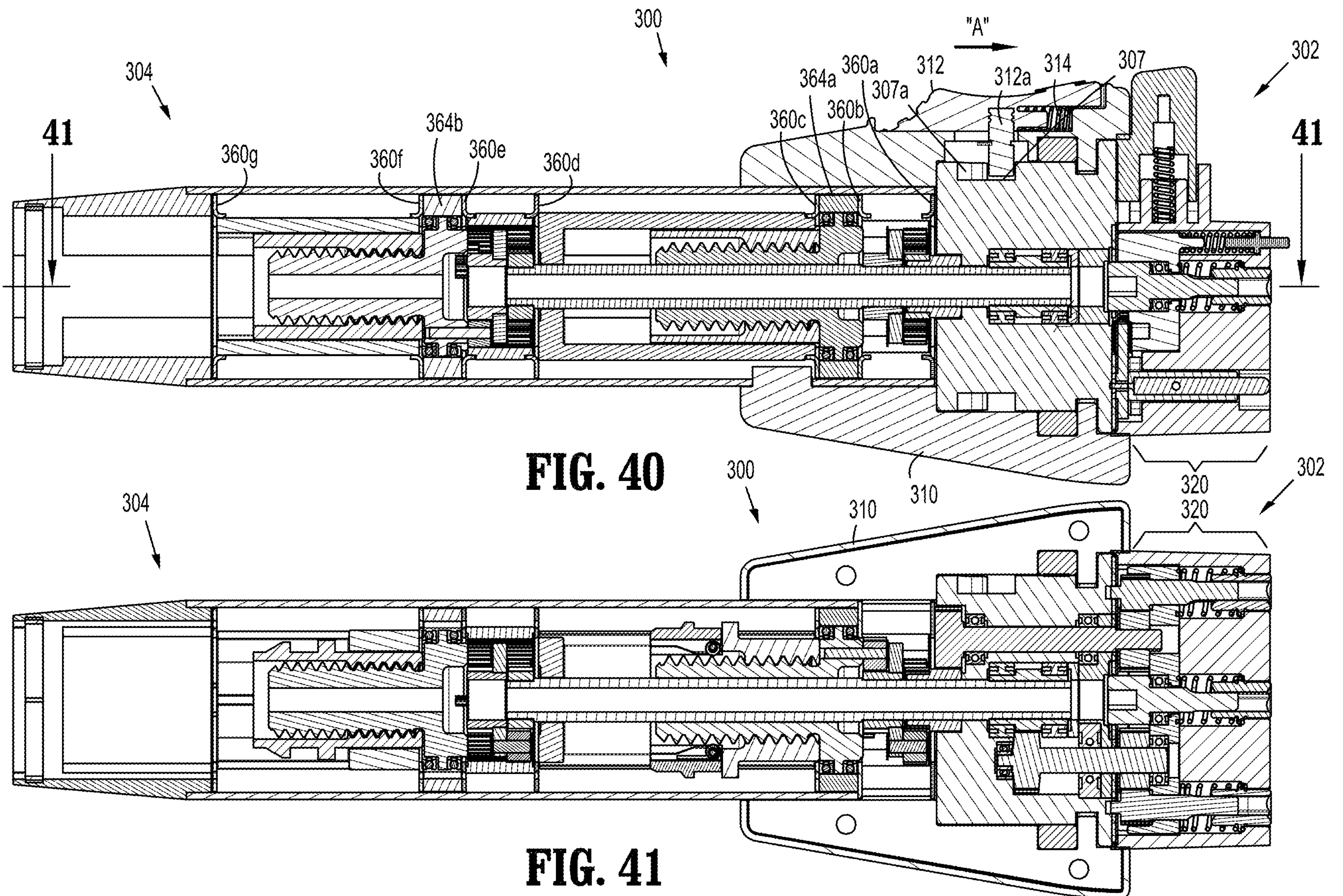
FIG. 40 is a cross-sectional side view taken along line 40-40 of FIG. 36.
FIG. 41 is a cross-sectional side view taken along line 41-41 of FIG. 40.

With reference now to FIGS. 34 and 35, extension assembly 200 is connected to adapter assembly 100 by receiving proximal end 202 (FIG. 17) of extension assembly 200 within distal end 104 of adapter assembly 100. In particular, first and second connection extensions 220, 240, 222, 242 of respective inner and outer flexible band assemblies 210, 230 are received within sleeve 106 of adapter assembly 100 such that tabs 178 of pusher member 170 of first pusher assembly 160 of adapter assembly 100 are received within openings 241, 243 of respective first and second connection extensions 240, 242 of outer flexible band assembly 230 to secure outer flexible band assembly 230 with first pusher assembly 160 and tabs 198 of pusher member 190 of second pusher assembly 180 of adapter assembly 100 are received within openings 221, 223 of first and second connection extensions 221, 223 of inner flexible band assembly 210 to secure inner flexible band assembly 210 with second pusher assembly 180.

As noted above, adapter assembly 100 may include a drive shaft 108 (FIG. 3) that extends from distal end 104 of adapter assembly 100. Prior to receipt of proximal portion 202 of extension assembly 200 within distal end 104 of extension assembly 100, drive shaft 108 is removed from adapter assembly 100. As proximal portion 202 of extension assembly 200 is received within distal end 102 of adapter assembly 100, proximal end 286*a* (FIG. 17) of second drive shaft 286 (FIG. 17) is received within socket 145 of drive member 140 of drive transfer assembly 130 of extension assembly 100 (FIG. 12).

After extension assembly 200 is operably engaged with adapter assembly 100, and adapter assembly 100 is operably engaged with surgical device 10 (FIG. 1), loading unit 40 (FIG. 34) of end effector 30 (FIG. 34) may be attached to connector assembly 290 of extension assembly 200 and an anvil assembly 50 (FIG. 34) may be attached to distal end 274*b* of trocar 274 of extension assembly 200 in a conventional manner. During actuation of loading unit 40 and anvil assembly 50, longitudinal advancement of pusher member 190 of second pusher assembly 180 of adapter assembly 100, as described above, and as indicated by arrows "C" in FIG. 35A, causes longitudinal advancement of outer flexible band assembly 230 of extension assembly 200 and longitudinal advancement of pusher member 170 of first pusher assembly 160, as described above, and as indicated by arrows "D" in FIG. 35A, causes longitudinal advancement of inner flexible band assembly 210. Rotation of drive shaft 108 in a first direction, as described above, and as indicated by arrow "E", causes advancement of trocar 274 of extension assembly 200. Conversely, longitudinal retraction of pusher member 190 causes longitudinal retraction of outer flexible band assembly 230, longitudinal retraction of pusher member 170 causes longitudinal retraction of inner flexible band assembly 210, and rotation of drive shaft 108 in a second direction causes retraction of trocar 274 of extension assembly 200.

In embodiments, inner flexible band assembly 210 operably connects second pusher assembly 180 of adapter assembly 100 with a knife assembly (not shown) of loading unit 40 (FIG. 34) of end effector 30 (FIG. 34) attached to connector assembly 290 of extension assembly 200. Outer flexible band assembly 230 operably connects first pusher assembly 160 of adapter assembly 100 with a staple driver assembly (not shown) of loading unit 40. Trocar assembly 270 operably connects drive transfer assembly 130 of adapter assembly 100 to anvil assembly 50 (FIG. 34) of end effector 30 (FIG. 34). In this manner, operation of second pusher assembly 160 causes longitudinal movement of inner flexible band assembly 210 which causes longitudinal movement of the knife assembly, operation of first pusher assembly 180 causes longitudinal movement of outer flexible band assembly 230 which causes longitudinal movement of the staple driver assembly, and operation of drive transfer assembly 130 causes longitudinal movement of trocar 274 which causes longitudinal movement of anvil assembly 50 relative to loading unit 40.

By stacking first and second pusher assemblies 160, 180 of adapter assembly 100, as described, and positioning the drive shaft 108 of the transfer assembly 130 through first and second pusher assemblies 160, 180, adapter assembly 100 can perform three functions through an access port or other opening (not shown) having a small diameter, e.g., 21 mm. Similarly, by configuring inner flexible band assembly 210 within outer flexible band assembly 230 and receiving trocar assembly 270 through the inner and outer flexible band assemblies 210, 230, extension assembly 200 can perform three functions through an access port or other opening (not shown) having a small diameter, e.g., 21 mm.

With reference to FIGS. 36-41, an adapter assembly according to another embodiment of the present disclosure is shown as adapter assembly 300. Adapter assembly 300 is substantially similar to adapter assembly 100 described hereinabove and will only be described as relates to the differences therebetween.

As will become apparent from the following description, the configuration of adapter assembly 300 permits rotation of a distal portion 304 of adapter assembly 300 about a longitudinal axis "x" (FIG. 36), relative to a proximal portion 302 of adapter assembly 300. In this manner, an end effector, e.g. end effector 30 (FIG. 34) secured to distal portion 304 of adapter assembly 300 or an end effector secured to an extension assembly, e.g., extension assembly 200 (FIG. 17) which is secured to distal portion 304 of adapter assembly 300 is rotatable about longitudinal axis "x" independent of movement of the surgical device (not shown) to which adapter assembly 300 is attached.

Adapter assembly 300 includes a base 306 and a support structure 308 rotatable relative to base 306 along longitudinal axis "x" of adapter assembly 300. A rotation handle 310 is rotatably secured to base 306 and fixedly secured to a proximal end of support structure 308. Rotation handle 310 permits longitudinal rotation of distal portion 304 of adapter assembly 300 relative to proximal end 302 of adapter assembly 300. As will be described in further detail below, a latch 312 is mounted to rotation handle 310 and selectively secures rotation handle 310 in a fixed longitudinal position.

Proximal portion 302 of adapter assembly 300 includes a drive coupling assembly 320 and a drive transfer assembly 330 operably connected to drive coupling assembly 320. Distal portion 304 of adapter assembly 300 includes a first pusher assembly 340 operably connected to drive transfer assembly 330, and a second pusher assembly 350 operably connected to drive transfer assembly 330. Drive coupling assembly 320 and drive transfer assembly 330 are mounted within base 306, and thus, remain rotationally fixed relative to the surgical device (not shown) to which adapter assembly 300 is attached. First pusher assembly 340 and second pusher assembly 350 are mounted within support structure 308, and thus, are rotatable relative to the surgical device (not shown) to which adapter assembly 300 is attached.

Drive coupling assembly 320 is configured to selectively secure adapter assembly 300 to a surgical device (not shown). For a detailed description of an exemplary surgical device and drive coupling assembly, please refer to commonly owned U.S. Provisional Patent Application Ser. No. 61/913,572, filed Dec. 9, 2013, the content of which is incorporated by reference herein in its entirety.

Rotation handle 310 is rotatably secured to base 306. Latch 312 includes a pin 312*a* (FIG. 40) configured to lock rotation handle 310 relative to base 306. In particular, pin 312a of latch 312 is received within a slot 307 formed in base 306 and is biased distally by a spring 314 into a notch 307a (FIG. 40) formed in base 306 and in communication with slot 307 to lock rotation handle 310 relative to base 306. Proximal movement of latch 312, as indicated by arrow "F" in FIG. 36, retracts pin 312*a* from within notch 307*a* to permit rotation of rotation handle 310 relative to base 306. In embodiments, base 306 defines a second notch (not shown) diametrically opposed to notch 307*a* for locking rotation handle 310 in a first longitudinal orientation when pin 312a of latch 312 is received within notch 307*a* and in a second longitudinal orientation that is one-hundred eighty degrees) (180°) rotated from the first longitudinal orientation when pin 312*a* of latch 312 is received within the second notch. Alternatively, it is envisioned that base 306 may define a number of notches radially spaced about base 306 and in communication with slot 307 that permit rotation handle 310 to be locked in a number of longitudinal orientations relative to base 306.

Drive transfer assembly 330, first drive pusher assembly 340, and second drive pusher assembly 350 of adapter assembly 300 are substantially identical to respective drive transfer assembly 130, first drive pusher assembly 160, and second drive pusher assembly 180 of adapter assembly 100 described hereinabove, and therefore, will only be described as relates to the differences therebetween.

Support structure 308 is fixedly received about first and second drive pusher assemblies 340, 350 and rotatably relative to base 306. As noted above, rotation knob 310 is fixedly secured to the proximal end of support structure 308 to facilitate rotation of support structure 308 relative to base 306. Support structure 308 is retained with outer sleeve 305 of adapter assembly 300 and is configured to maintain axial alignment of first and second drive pusher assemblies 340, 350. Support structure 308 may also reduce the cost of adapter assembly 300 when compared to the cost of adapter assembly 100.

Support structure 308 respectively includes first, second, third, fourth, fifth, sixth, and seventh plates 360*a*, 360*b*, 360*c*, 360*d*, 360*e*, 360*f*, 360*g*, first and second pluralities of tubular supports 362*a*, 362*b*, first and second support rings 364*a*, 364*b*, first and second plurality of ribs 366*a*, 366*b*, and a plurality of rivets 368. From proximal to distal, first and second plates 360*a*, 360*b* are maintained in spaced apart relation to each other by the first plurality of tubular supports 362*a*, second and third plates 360*b*, 360*c* are maintained in spaced apart relation to each other by first support ring 364*a*, third and fourth plates 360*c*, 360*d* are maintained in spaced apart relation to each other by first plurality of support ribs 366*a*, fourth and fifth plates 360*d*, 360*e* are maintained in spaced apart relation to each other by second plurality of tubular supports 362*b*, fifth and sixth plates 360*e*, 360*f* are maintained in spaced apart relation to each other by a second support ring 364*b*, and sixth and seventh plates 360*f*, 360*g* are maintained in spaced apart relation to each other by second plurality of support ribs 366*b*. First, second, third, fourth, fifth, sixth, and seventh plates 360*a-g* are held together by a plurality of rivets 368 secured to first and seventh plates 360*a*, 360*g* and extending through second, third, fourth, fifth, and sixth plates 360*b*-360*f*, first and second support rings 364*a*, 364*b*, and respective first and second plurality of tubular support 362*a*, 362*b*.

Adapter assembly 300 operates in a substantially similar manner to adapter assembly 100 described hereinabove. In addition, as described in detail above, adapter assembly 300 is configured to permit rotation of an end effector, e.g., end effector 30 (FIG. 34) attached to adapter assembly 300 or attached to an extension assembly that is attached to adapter assembly 300 to be selectively rotated about longitudinal axis “x” (FIG. 36) during use.

Figure 42:
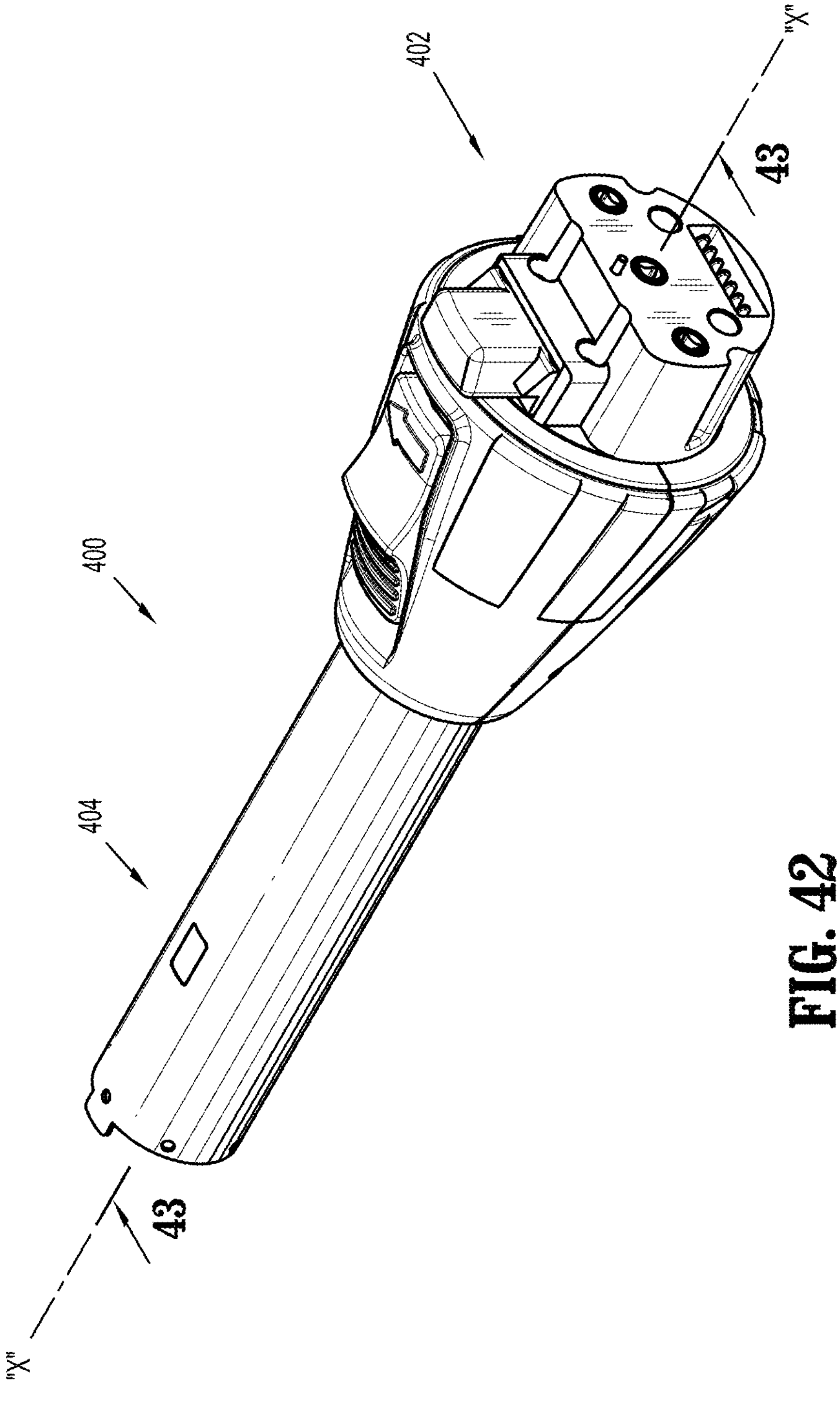
FIG. 42 is a rear, perspective view of an adapter assembly according to yet another embodiment of the present disclosure.
Figures 43, 44:
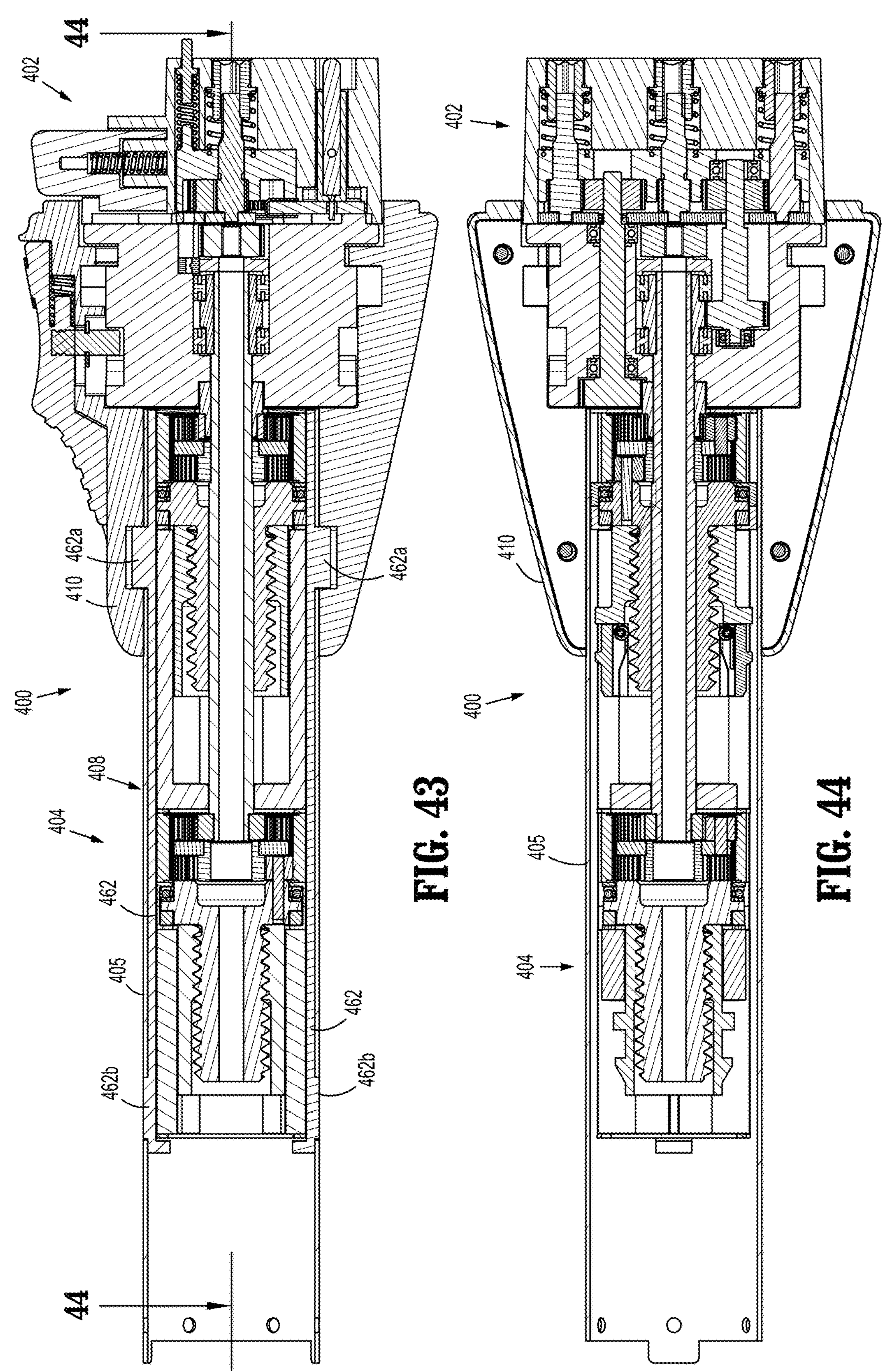
FIG. 43 is a cross-sectional side view taken along line 43-43 of FIG. 42.
FIG. 44 is a cross-sectional side view taken along line 44-44 of FIG. 42.
Figure 45:
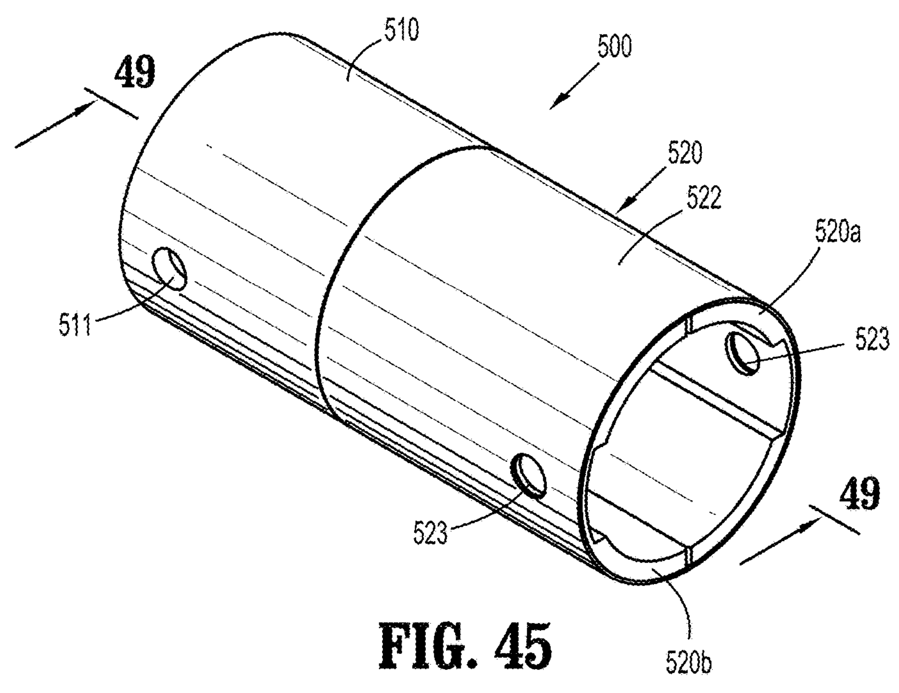
FIG. 45 is a perspective view of a connector assembly according to an embodiment of the present disclosure.
Figure 46:
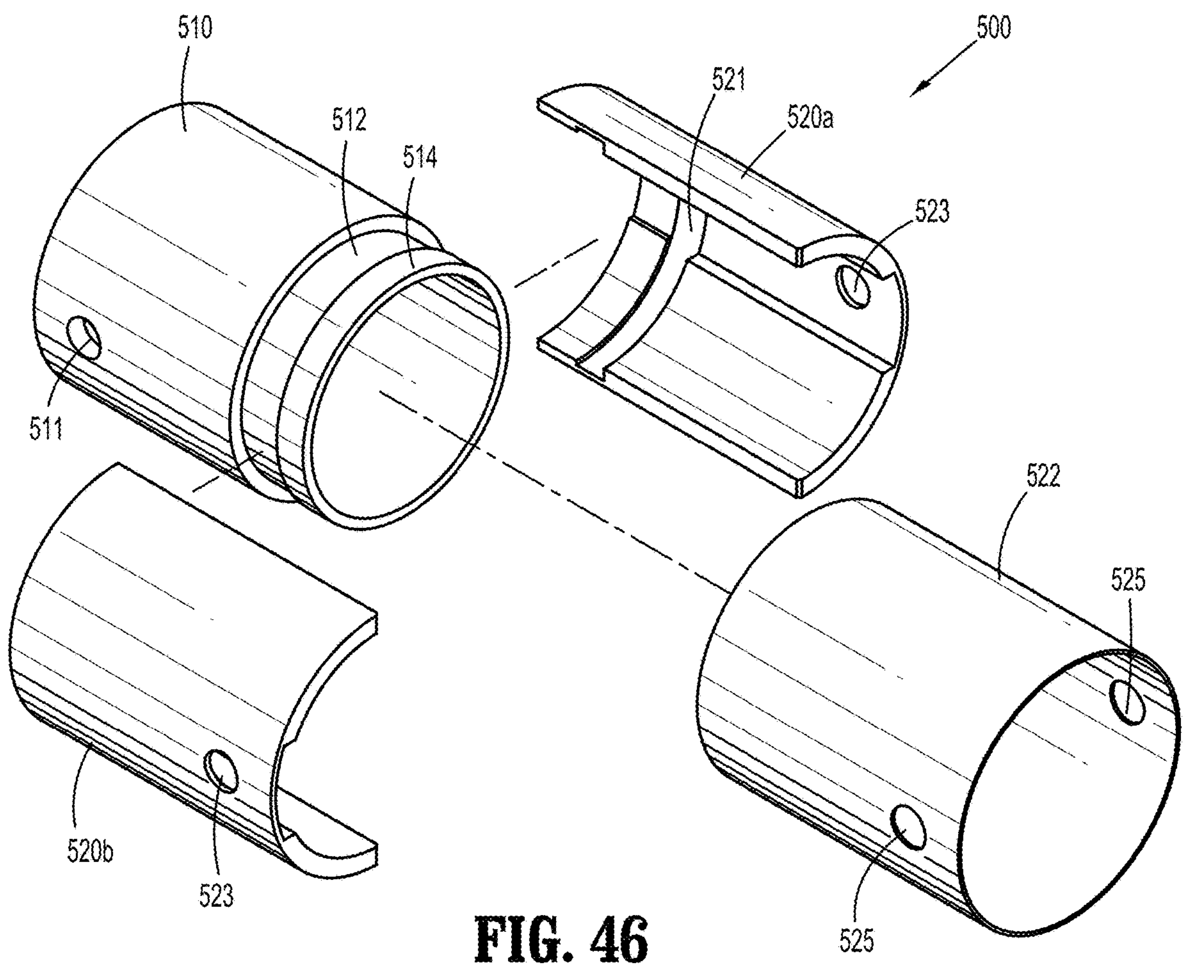
FIG. 46 is an exploded perspective view of the connector assembly of FIG. 45.
Figures 47, 48, 49:
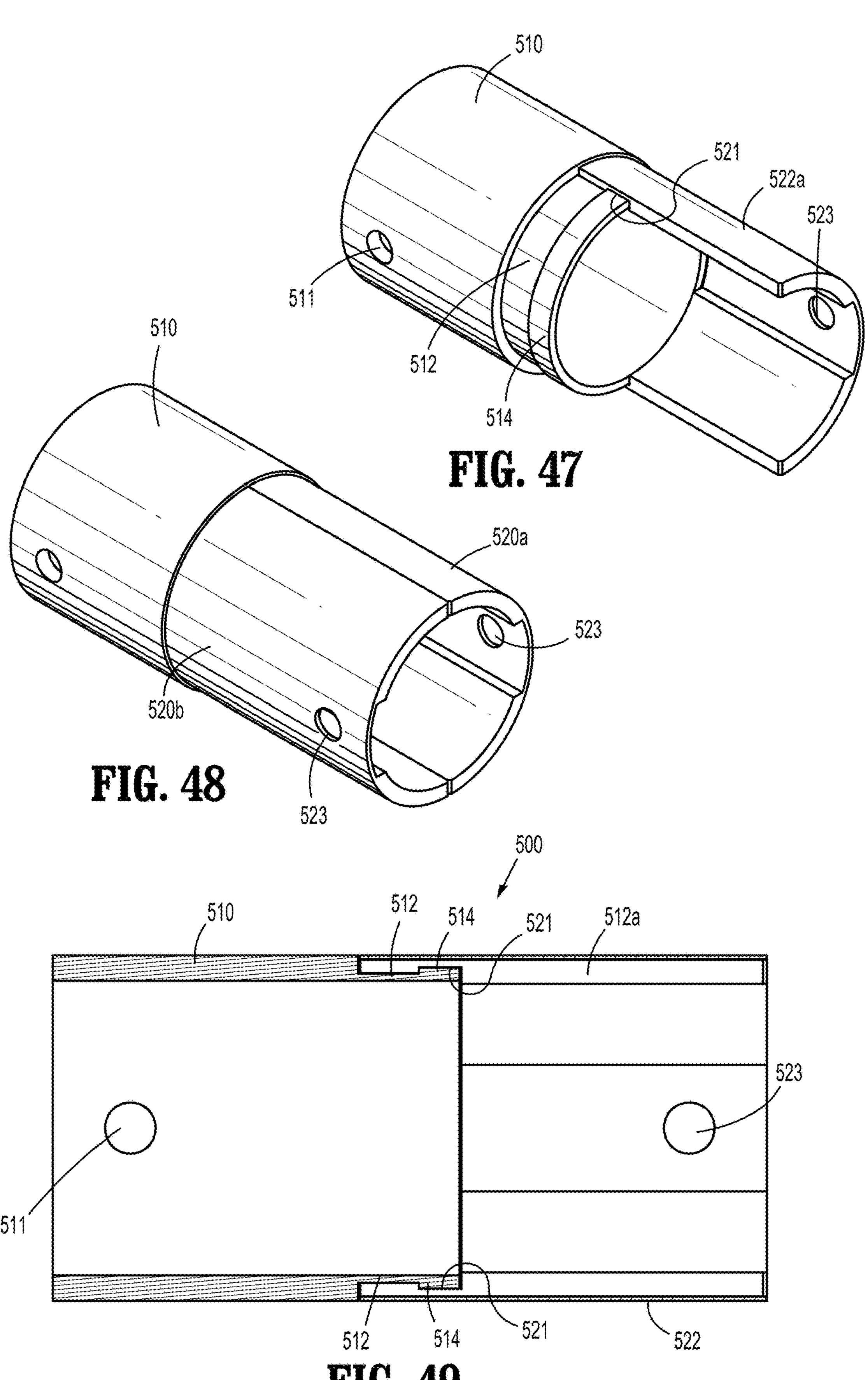
FIG. 47 is a perspective view of the connector assembly of FIG. 45 with a sleeve and first section of a tubular extension removed.
FIG. 48 is a perspective view of the connector assembly of FIG. 45 with the sleeve removed.
FIG. 49 is a cross-sectional side view taken along line 49-49 of FIG. 45.

With reference now to FIGS. 42-44, an adapter assembly according to another embodiment of the present disclosure is shown generally as adapter assembly 400. Adapter assembly 400 is substantially similar to adapter assemblies 100 and 300 described hereinabove, and therefore will only be described as relates to the differences therebetween.

Adapter assembly 400 includes a proximal portion 402 and a distal portion 404 rotatable along a longitudinal axis “x” relative to proximal portion 402. Distal portion 404 includes a support structure 408 secured to outer sleeve 405 and formed about first and second pusher assemblies 440, 450. Support structure 408 includes a plurality of reinforcing members 462 extending substantially the length of outer sleeve 405. Reinforcing members 462 each include a proximal tab 462*a* and a distal tab 462*b* which extend through outer sleeve 405 to secure reinforcing member 462 within outer sleeve 405. Proximal tabs 462*a* of reinforcing members 462 are further configured to engage a rotation knob 410 of adapter assembly 400. Adapter assembly 400 may include annular plates (not shown) positioned radially inward of reinforcing members 462 that maintain proximal and distal tabs 462a, 462b of reinforcing members 462 in engagement with outer sleeve 405. The annular plates may also provide structure support to distal portion 404 of adapter assembly 400. The configuration of adapter assembly 400 allows for a single tube, e.g. outer sleeve 405, for containing the drive components. With reference to FIGS. 45-49, a connection assembly according to an embodiment of the present disclosure is shown generally as connection assembly 500. As shown and will be described, connection assembly 500 is configured to be attached to first and second tubular bodies (not shown) for connecting the first tubular body, i.e., adapter assembly 100 (FIG. 3), 300 (FIG. 36), 400 (FIG. 42), to the second tubular body, i.e., extension assembly 200 (FIG. 17). It is envisioned, however, that the aspects of the present disclosure may be incorporated directly into the first and second tubular bodies to permit connection of the first tubular body directly to the second tubular body.

Connection assembly 500 includes a tubular base 510 and a tubular extension 520 formed of first and second sections 520*a*, 520*b* and an outer sleeve 522. As shown, tubular base 510 defines a pair of openings 511 for securing tubular base 510 to a first tubular body (not shown). Alternatively, tubular base 510 may include only a single opening, one or more tabs (not shown), and/or one or more slots (not shown), for securing tubular base 510 to the first tubular body (not shown). A flange 512 extends from a first end of tubular base 510 and includes an annular rim 514 extending thereabout.

First and second sections 520*a*, 520*b* of tubular extension 520 are substantially similar to one another and each define a groove 521 formed along an inner first surface thereof. Each of first and second section 520*a*, 520*b* of tubular extension 520 is configured to be received about flange 512 of tubular base 510 such that rim 514 of tubular base 510 is received within grooves 521 of first and second sections 520*a*, 520*b* of tubular extension 520. Once first and second sections 520*a*, 520*b* of tubular extension 520 are received about flange 512 of tubular base 510, outer sleeve 522 of tubular extension 520 is received about first and second sections 520*a*, 520*b* of tubular extension 520 to secure tubular extension 520 to tubular base 510.

As shown, each of first and second sections 520*a*, 520*b* of tubular extension 520 define an opening 523 configured to be aligned with a pair of openings 525 in outer sleeve 522 to secure outer sleeve 522 to first and second sections 520*a*, 520*b*. Either or both of first and second sections 520*a*, 520*b* and outer sleeve 522 may include one or more tabs, and/or one or more slots for securing outer sleeve 522 about first and second extensions. Alternatively, outer sleeve 522 may be secured to first and second sections 520*a*, 520*b* in any suitable manner.

Outer sleeve 522 may be selectively secured about first and second extensions for selective removal of outer sleeve 522 from about first and second sections 520*a*, 520*b* to permit separation of tubular extension 520 from tubular base 510. Alternatively, outer sleeve 522 may be permanently secured about first and second section to prevent tubular extension 520 from being separated from tubular base 510. As noted above, although tubular base 510 and tubular extension 520 are shown and described as forming an independent connection assembly 500, it is envisioned that tubular base 510 may be formed on a first tubular member, i.e., adapter assembly 100 (FIG. 3) and tubular extension 520 may be formed on a second tubular member, i.e., extension assembly 200 (FIG. 17) such that the first tubular member may be directly connected to the second tubular member.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to a surgical instrument, comprising:

a base;

a support structure rotatable relative to the base along a longitudinal axis, wherein the support structure includes a plurality of plates and a plurality of tubular supports maintaining the plates in spaced apart relation;

a rotation handle rotatably secured to the base and fixedly secured to a proximal end of the support structure, wherein rotation of the rotation handle causes rotation of a distal portion of the adapter assembly relative to a proximal end of the adapter assembly;

a latch, mounted to an outer surface of the rotation handle, the latch including a pin biased into engagement with a notch formed in the base to selectively lock the rotation handle in a fixed longitudinal position;

a drive coupling assembly disposed within the base and configured for operable connection to the surgical instrument;

a drive transfer assembly disposed within the base and operably connected to the drive coupling assembly; and first and second pusher assemblies disposed within the support structure and operably connected to the drive transfer assembly.

2. The adapter assembly of claim 1, wherein the latch includes a spring biasing the pin distally into the notch.

3. The adapter assembly of claim 1, wherein the base defines a second notch diametrically opposed to the notch to lock the rotation handle in a 180 degree rotated position.

4. An adapter assembly for operably connecting an end effector to a surgical instrument, comprising:

a base;

a support structure rotatable relative to the base along a longitudinal axis, the support structure including:

a plurality of plates;

a plurality of tubular supports maintaining the plates in spaced apart relation;

at least one support ring positioned between adjacent plates;

a plurality of ribs positioned between adjacent plates; and a plurality of rivets securing the plates, tubular supports, support rings, and ribs together;

a drive coupling assembly disposed within the base; and first and second pusher assemblies disposed within the support structure.

5. The adapter assembly of claim 4, wherein the plurality of plates includes first, second, third, fourth, fifth, sixth, and seventh plates.

6. The adapter assembly of claim 5, wherein the first and second plates are maintained in spaced apart relation by the plurality of tubular supports.

7. The adapter assembly of claim 5, wherein the support structure further includes a first support ring positioned between the second and third plates.

8. The adapter assembly of claim 7, wherein the support structure includes a second support ring positioned between the fifth and sixth plates.

9. The adapter assembly of claim 5, wherein the plurality of ribs includes a first plurality of ribs positioned between the third and fourth plates.

10. The adapter assembly of claim 4, further comprising an outer sleeve retaining the support structure.

11. The adapter assembly of claim 4, further comprising a drive transfer assembly, operably connected to the drive coupling assembly, wherein the drive transfer assembly includes a first rotatable distal drive shaft operably connected to the first pusher assembly.

12. An adapter assembly for operably connecting an end effector to a surgical instrument, comprising:

a proximal portion;

a distal portion rotatable relative to the proximal portion along a longitudinal axis;

an outer sleeve;

a support structure secured within the outer sleeve and rotatable with the distal portion relative to the proximal portion, the support structure including a plurality of proximal tabs and a distal tabs extending radially and at least partially through the outer sleeve; and first and second pusher assemblies disposed within the support structure and configured to convert rotational input from a drive transfer assembly into longitudinal movement, wherein the first and second pusher assemblies are rotatable relative to the surgical instrument.

13. The adapter assembly of claim 12, wherein the proximal tabs and distal tabs engage the outer sleeve.

14. The adapter assembly of claim 12, further comprising annular plates positioned to maintain the proximal and distal tabs in engagement with the outer sleeve.

15. The adapter assembly of claim 12, wherein the support structure is formed within a single outer sleeve.

16. The adapter assembly of claim 12, wherein the support structure includes a rotation handle rotatably secured to the proximal portion, wherein rotation of the rotation handle causes rotation of the distal portion.

17. The adapter assembly of claim 12, wherein the first and second pusher assemblies are operably connected to the drive transfer assembly disposed within the proximal portion.

18. The adapter assembly of claim 12, wherein the outer sleeve is a single tube comprising the support structure and the first and second pusher assemblies.

* * * * *